United States Patent
Swarup et al.

(10) Patent No.: US 12,064,197 B2
(45) Date of Patent: Aug. 20, 2024

(54) SYSTEM AND METHODS FOR POSITIONING A MANIPULATOR ARM BY CLUTCHING WITHIN A NULL-PERPENDICULAR SPACE CONCURRENT WITH NULL-SPACE MOVEMENT

(71) Applicant: Intuitive Surgical Operations, Inc., Sunnyvale, CA (US)

(72) Inventors: Nitish Swarup, Sunnyvale, CA (US); Arjang M. Hourtash, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/122,896

(22) Filed: Mar. 17, 2023

(65) Prior Publication Data

US 2023/0210617 A1    Jul. 6, 2023

Related U.S. Application Data

(63) Continuation of application No. 17/390,722, filed on Jul. 30, 2021, now Pat. No. 11,638,619, which is a
(Continued)

(51) Int. Cl.
*A61B 34/30* (2016.01)
*A61B 34/37* (2016.01)
(Continued)

(52) U.S. Cl.
CPC .............. *A61B 34/30* (2016.02); *A61B 34/37* (2016.02); *B25J 9/1607* (2013.01); *B25J 9/1638* (2013.01); *B25J 9/1666* (2013.01); *B25J 18/007* (2013.01)

(58) Field of Classification Search
CPC ......... A61B 34/30; A61B 34/37; A61B 34/32; B25J 9/1607; B25J 9/1638; B25J 9/1666; B25J 18/007
(Continued)

(56) References Cited

U.S. PATENT DOCUMENTS

| 5,214,749 A | 5/1993 | Brown |
| 5,430,643 A | 7/1995 | Seraji |

(Continued)

FOREIGN PATENT DOCUMENTS

| EP | 2332484 A2 | 6/2011 |
| EP | 2444006 A2 | 4/2012 |

(Continued)

OTHER PUBLICATIONS

Baerlocher, P. et al., "Task Priority Formulations for the Kinematic Control of Highly Redundant Articulated Structures," IEEE/RSJ International Conference on Intelligent Robots and Systems, Oct. 1998, vol. 1, pp. 323-329.
(Continued)

*Primary Examiner* — David Luo
(74) *Attorney, Agent, or Firm* — Osha Bergman Watanabe & Burton LLP

(57) ABSTRACT

Devices, systems, and methods for positioning an end effector or remote center of a manipulator arm by floating a first set of joints within a null-perpendicular joint velocity subspace and providing a desired state or movement of a proximal portion of a manipulator arm concurrent with end effector positioning by driving a second set of joints within a null-space orthogonal to the null-perpendicular space. Methods include floating a first set of joints within a null-perpendicular space to allow manual positioning of one or both of a remote center or end effector position within a work space and driving a second set of joints according to
(Continued)

an auxiliary movement calculated within a null-space according to a desired state or movement of the manipulator arm during the floating of the joints. Various configurations for devices and systems utilizing such methods are provided herein.

25 Claims, 20 Drawing Sheets

Related U.S. Application Data continuation of application No. 16/859,892, filed on Apr. 27, 2020, now Pat. No. 11,109,924, which is a continuation of application No. 16/284,815, filed on Feb. 25, 2019, now Pat. No. 10,687,908, which is a continuation of application No. 15/885,685, filed on Jan. 31, 2018, now Pat. No. 10,251,715, which is a continuation of application No. 15/235,103, filed on Aug. 12, 2016, now Pat. No. 9,907,619, which is a continuation of application No. 14/218,788, filed on Mar. 18, 2014, now Pat. No. 9,415,510.

(60) Provisional application No. 61/799,920, filed on Mar. 15, 2013.

(51) Int. Cl.
*B25J 9/16* (2006.01)
*B25J 18/00* (2006.01)

(58) Field of Classification Search
USPC .......................................... 318/560; 700/255
See application file for complete search history.

(56) References Cited

U.S. PATENT DOCUMENTS

| | | | |
|---|---|---|---|
| 6,963,792 B1 | 11/2005 | Green | |
| 7,699,835 B2 | 4/2010 | Lee et al. | |
| 7,819,859 B2 | 10/2010 | Prisco et al. | |
| 8,004,229 B2 | 8/2011 | Nowlin et al. | |
| 8,005,571 B2 * | 8/2011 | Sutherland | A61B 34/37 |
| | | | 318/568.22 |
| 8,332,072 B1 | 12/2012 | Schaible et al. | |
| 8,541,970 B2 | 9/2013 | Nowlin et al. | |
| 8,624,537 B2 | 1/2014 | Nowlin et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 9,233,467 B2 | 1/2016 | Tsusaka et al. | |
| 9,415,510 B2 | 8/2016 | Hourtash et al. | |
| 9,907,619 B2 | 3/2018 | Hourtash et al. | |
| 10,251,715 B2 | 4/2019 | Hourtash et al. | |
| 10,687,908 B2 | 6/2020 | Hourtash et al. | |
| 11,109,924 B2 | 9/2021 | Swarup et al. | |
| 2006/0243085 A1 | 11/2006 | Hannaford et al. | |
| 2007/0043338 A1 | 2/2007 | Moll et al. | |
| 2009/0088775 A1 | 4/2009 | Swarup et al. | |
| 2011/0040306 A1 | 2/2011 | Prisco | |
| 2011/0202068 A1 | 8/2011 | Diolaiti et al. | |
| 2014/0052155 A1 | 2/2014 | Hourtash et al. | |
| 2021/0353375 A1 | 11/2021 | Swarup et al. | |

FOREIGN PATENT DOCUMENTS

| | | |
|---|---|---|
| JP | 2006334774 A | 12/2006 |
| WO | WO-2006124390 A2 | 11/2006 |
| WO | WO-2013078529 A1 | 6/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146113 A1 | 9/2014 |
| WO | WO-2016044574 A1 | 3/2016 |

OTHER PUBLICATIONS

Extended European Search Report for Application No. EP22190871.8, mailed on Feb. 23, 2023, 13 pages.

Funda J., et al., "Constrained Cartesian Motion Control for Teleoperated Surgical Robots," IEEE Transactions on Robotics and Automation, IEEE, Jun. 1996, vol. 12 (3), pp. 453-465.

International Search Report and Written Opinion for Application No. PCT/US2014/31082, mailed on Jul. 1, 2014, 16 pages.

Jamshidi et al., "Robotics and Manufacturing—Recent Trends in Research, Education and Applications," Proceedings of the Second International Symposium of Robotics and Manufacturing: Research, Education, and Applications, ASME Press, Nov. 16-18, 1988, 17 pages.

Maciejewski A.A., et al., "Obstacle Avoidance for Kinematically Redundant Manipulators in Dynamically Varying Environments," International Journal of Robotics Research, Sep. 1985, vol. 4 (3), pp. 109-116.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

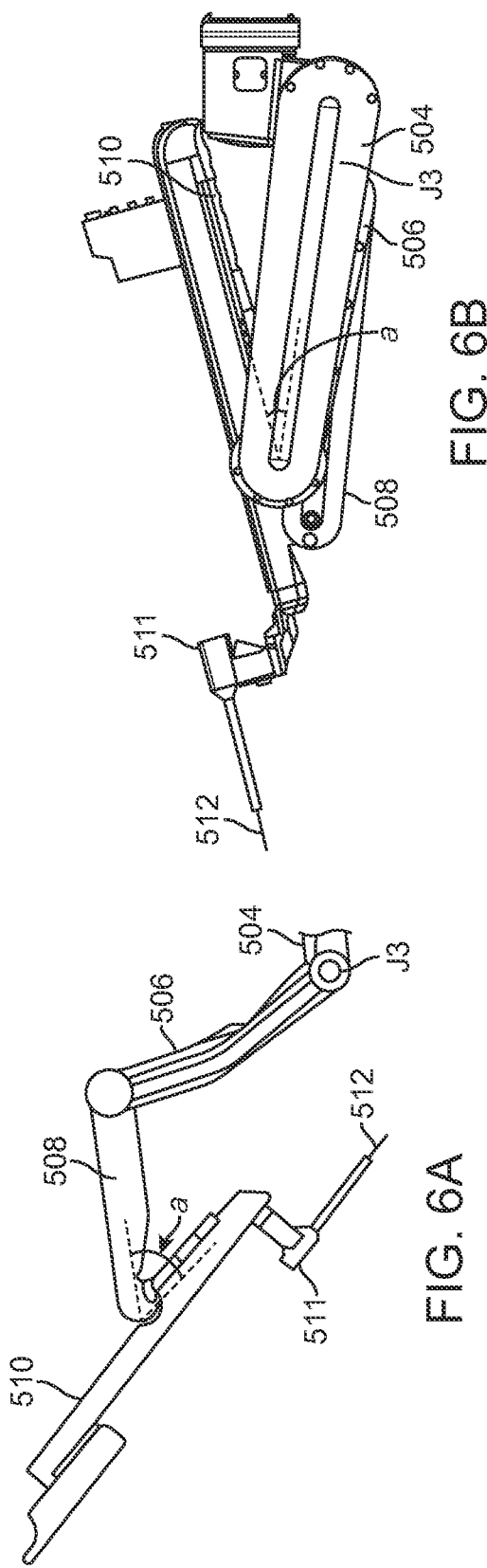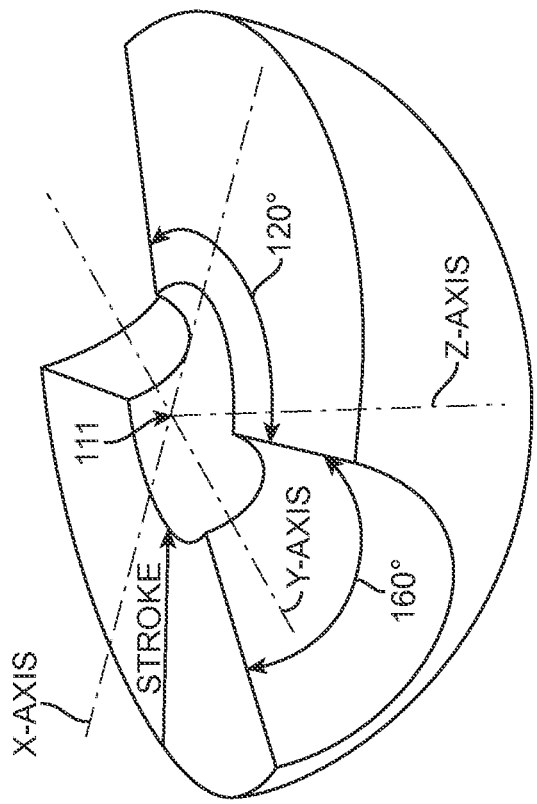
FIG. 6A
FIG. 6B
FIG. 6C

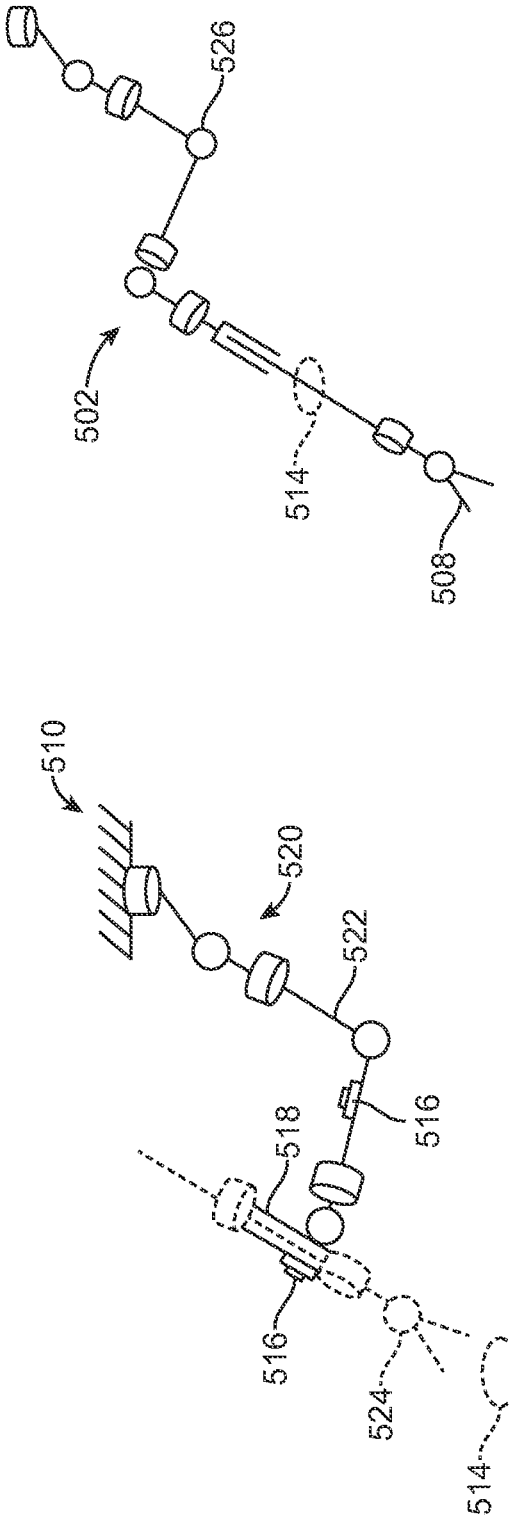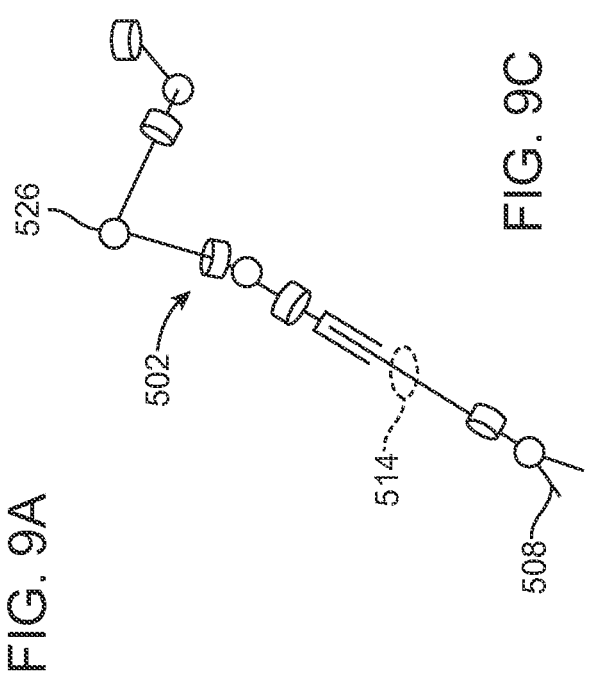
FIG. 9A
FIG. 9B
FIG. 9C

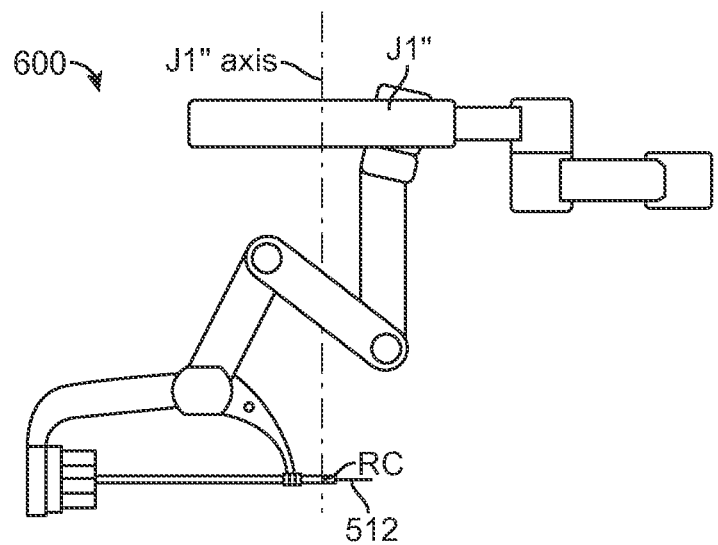
FIG. 12A
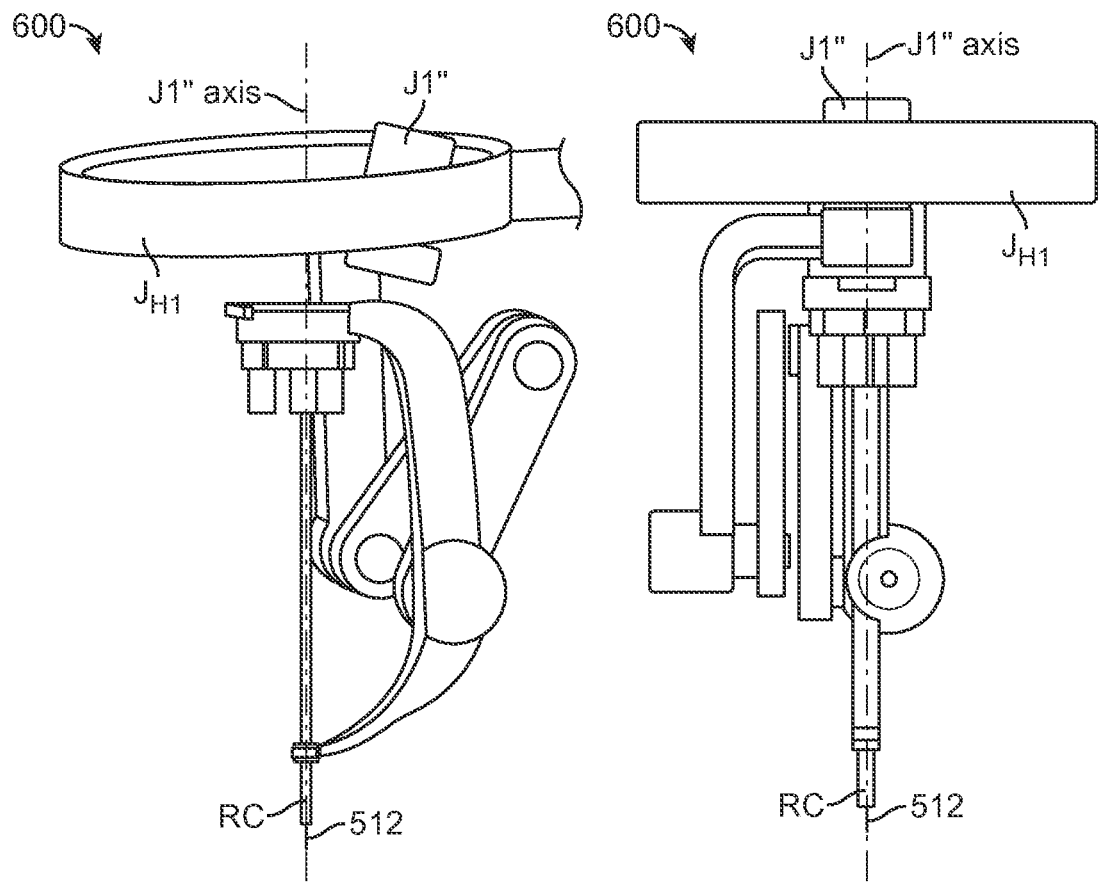
FIG. 12B
FIG. 12C

SYSTEM AND METHODS FOR POSITIONING A MANIPULATOR ARM BY CLUTCHING WITHIN A NULL-PERPENDICULAR SPACE CONCURRENT WITH NULL-SPACE MOVEMENT

CROSS-REFERENCES TO RELATED APPLICATIONS

This application is a continuation of and claims the benefit of priority under 35 U.S.C. § 120 to U.S. patent application Ser. No. 17/390,722, filed Jul. 30, 2021, which is a continuation of an claims the benefit of priority under 35 U.S.C. § 120 to U.S. patent application Ser. No. 16/859,892, filed Apr. 27, 2020, which is a continuation of and claims the benefit of priority under 35 U.S.C. § 120 to U.S. patent application Ser. No. 16/284,815, filed on Feb. 25, 2019, which is a continuation of and claims the benefit of priority under 35 U.S.C. § 120 to U.S. patent application Ser. No. 15/885,685, filed on Jan. 31, 2018, which is a continuation of and claims the benefit of priority under 35 U.S.C. § 120 to U.S. patent application Ser. No. 15/235,103, filed on Aug. 12, 2016, which is a continuation of and claims the benefit of priority under 35 U.S.C. § 120 to U.S. patent application Ser. No. 14/218,788, filed on Mar. 18, 2014, which claims the benefit of priority under 35 U.S.C. § 119(e) to U.S. Provisional Patent Application Ser. No. 61/799,920, filed on Mar. 15, 2013, each of which is incorporated by referenced herein in its entirety.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body, and can also increase the importance of avoiding excessive movement of the manipulators arm for certain tasks.

For these and other reasons, it would be advantageous to provide improved devices, systems, and methods for surgery, robotic surgery, and other robotic applications, and it would be particularly beneficial if these improved technologies provided the ability to provide more consistent and predictable movement of the manipulator arm during set-up or positioning of the manipulator. It would be further desirable to provide such improvements while increasing the range of motion of the instruments for at least some tasks and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. In one aspect, the invention provides improved movement of the manipulator arm by floating one or more joints within a null-perpendicular space to allow a distal portion of the manipulator arm to be repositioned, such as the distal end effector and/or remote center, while one or more joints are driven within a null-space to effect various other tasks or desired movements, such as collision avoidance or driving the arm toward a desired pose.

In one aspect, the robotic surgical system may utilize one or more clutch modes in which one or more joints are allowed to float along one or more axes (e.g. one or more degrees-of-freedom) within a joint velocity sub-space that results in movement of a distal portion of the manipulator, such as an end effector or distal end effector or a remote center about which an instrument shaft of the end effector pivots adjacent a minimally invasive aperture during surgery. This joint velocity sub-space is referred to as a null-perpendicular space, which is orthogonal to a null-space in which movement of the joints results in no change in state of the end effector and/or remote center. Since the manipulator arm is highly configurable, often including redundant joints such that a range of configurations and joints states are available for a given state of the end effector or remote center, movement of distal portion, such as an end effector, during set-up may result in undesirable movement of proximal portions of the manipulator arm resulting in poorly conditioned configurations or collisions between the manipulator arm and adjacent arms or personnel. For example, when inserting or positioning the tool tip or distal end effector of the manipulator within a cannula at the minimally invasive aperture before surgery, referred to herein as "docking," movement of the tool tip or end effector may results in undesirable movement of the more proximal portions of the manipulator arm. Thus, in one aspect, the invention provides improved movement of the manipulator by floating of one or more joints within the null-perpendicular space so that a user or patient side assistance can manually backdrive or reposition the end effector and/or the remote center during surgery, while movement of one or more other joints of the manipulator are driven within a null-space so as to provide improved movement of proximal portions of the manipulator arm by effecting various other tasks, such as collision avoidance, movement toward a desired pose, or movement according to various algorithms using the null space (the null-space moving with the end effector or remote center). This aspect simplifies set-up of the manipulator arm by allowing the patient-side assistant to "dock" the end effector within the cannula to prepare for surgery without driving or manipulating each other joint of the manipulator arm. This aspect is particularly useful in highly configurable manipulator arms, especially manipulator arms having redundant joints and manipulator arms utilizing a Jacobian based controller in which the primary calculations of the one or more joints are based on velocities rather than positions. These features may be utilized as a clutch feature or clutch mode (e.g. null-perpendicular float clutch) separately or in combination with various other clutching modes or any of the movements described herein. In addition, various aspects of the feature described above may be incorporated into one or more of the movements or modes described herein.

In some embodiments, a manipulator arm may include additional redundant joints that allow for various types of movements within a null-space, such as an auxiliary movement to avoid collisions, move toward a desired pose or to improve conditioning of the joints. In some embodiments, rather than relying on robotic devices that are mechanically constrained to pivot a tool about a fixed point in space, or robotic devices having passive joints which passively pivot about the tissues of a minimally invasive aperture, the present invention may calculate a motion that includes pivoting a link of the manipulator linkage about an aperture site. The degrees of freedom of the robotic linkages supporting the end effectors can allow the linkage to move throughout a range of configurations for a given end effector position, and the systems may drive the linkages to configurations which inhibit collisions involving one or more moving robotic structures. Set-up of highly flexible robotic linkages can be facilitated by processors which drive one or more joints of the linkage while the linkage is being manually positioned. Joint state sensors may be used to sense the manual backdriving movement of the floating joints for use in subsequent calculated joint movements.

In some embodiments, the invention allows for floating of a first set of joints to allow a patient-side assistant to manually backdrive the end effector or a remote center about which the end effector pivots to a desired position (e.g. location or alignment), while a second set of joints are driven to move the manipulator arm according to a desired state or movement. This aspect is accomplished by driving the first set of joints to float within a null-perpendicular space, while the second set of joints are driven within a null-space to effect one or more auxiliary tasks, such as collision avoidance, pose preference or other desired movements. The system senses movement of the floating joints during manual moving of the joints so as to determine the null-space in which the auxiliary movement of the second set of joints is calculated. It should be noted that the manipulator arm need not be mechanically "locked" to a set of constraints, if used, but rather a set of constraints can be utilized to direct movement of one or more joints of the manipulator arm when moving within the null-space.

In general, manually backdriving "floating joints" results in movement of various other joints in response and may result in undesirable movement of one or more joints, such as a collision between the manipulator arm and an adjacent arm or personnel, excessive movement, or movement toward an undesirable or a poorly conditioned pose. Manually backdriving a portion of the manipulator arm may utilize the same joints as used in manipulation of the end effector or may include various other selected joints or sets of joints. To provide improved movement of the manipulator arms, the redundant degrees of freedom may be used to determine a movement of the manipulator arm within a null-space concurrent with floating of the end effector or remote center. This may be accomplished by calculating joint movement of the plurality of the joints that "float" a first set of joints within a null-perpendicular space (i.e. joint velocity sub-space which results in movement of the end effector and/or remote center) and drive a second set of joints within a null space (i.e. joint velocity sub-space which maintains the position of the end effector and/or remote center, the null-space being orthogonal to the null-perpendicular space). Driving the second set of joints within the null-space allows for a repeatable and/or a desirable pattern of movement of the manipulator arm during position according to various algorithms in order to provide a desirable movement of a portion of the manipulator arm proximal the distal end effector during manual backdriving movement of the end effector. Typically, these features are included in a clutch mode to allow set-up or docking of the end effector before surgery or repositioning during surgery.

In one aspect, the movement of a manipulator arm having redundant degrees of freedom utilizes primary calculations based on joint velocities, such as by using a Jacobian based controller. As described herein, "floating" of the joints can generally be described as driving the joints so as to zero out the torques of the motors associated with movement of the joints (e.g. the controller memory may be continually reset to be equal to the input values so that the differences between the measured position and velocity and the commanded position and velocity are zero). It should be understood, however, that despite zeroing of the torques that would result in movement of the joint, various controller functions may still apply torques to the floating joints, such as may be used for friction compensation, gravity compensation, or the like, and such functions may remain unaltered during floating of the joints. As described herein, "servoing" the joints can generally be described as driving the joints with torques needed to maintain the desired state (e.g. position, alignment, etc.) so as to keep a portion of the manipulator, such as the distal end effector, "locked" in the desired state, without requiring any mechanical locking of any particular joint.

In many embodiments, first and second modules of the processor will be used differently in different control modes, such as a clutch mode, as described above and a tissue manipulator mode in which movement of the end effector according to a desired tissue manipulator movement is commanded by a surgeon. The tissue manipulator mode will often comprise a master/slave mode. The effective degrees of freedom of a particular joint may differ in the clutch mode as compared to the tissue manipulation mode. For example, a manipulator assembly providing the end effector with six or more mechanical degrees of freedom could be constrained so as to allow the end effector to be moved in space solely about a pivotal rotation center located where no joint is present. Alternatively, such an end effector might be translatable along an arbitrary plane skewed at an angle relative to every linkage and joint axis of the manipulator linkage assembly.

The manipulator assembly will often comprise a surgical tool or instrument having a shaft extending between a mounting interface and the end effector. The processor in a first mode may be configured to derive the desired movement of the end effector within an internal surgical space so that the shaft passes through a minimally invasive aperture site. Such a master/slave controller may, for example, comprise a velocity controller using an Jacobian pseudo-inverse matrix, which will often comprise a portion of the first module, or alternatively an augmented Jacobian. A second module may be used in the second or clutch mode, and may employ a projection of a clutch matrix with the inverse Jacobian matrix so as to provide combinations of joint velocities that are allowed in the clutch mode. The processor in the clutch mode may float a first set of joints within a joint velocity sub-space to allow manual articulation or movement of a first portion of the manipulator (e.g. end effector or associated remote center) to a desired position, while driving a second set of joints according to one or more null-space algorithms to provide a desired movement of another portion of the manipulator (e.g. a proximal portion between the proximal base and distal end effector) according to various null-space algorithms. In some embodiments, an orientation of the end effector (or some other structure of the manipulator) may be orientationally constrained by driving of the driven clutch joints while that structure is manually translated by backdriving to a new location.

In one aspect of the present invention, a redundant degrees of freedom (RDOF) surgical robotic system with manipulate input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. In response to receiving a tissue manipulation command to move the end effector with a desired movement, the system calculates end effector displacing movement of the joints by calculating joint velocities within a null-perpendicular-space of the Jacobian orthogonal to the null-space, and drives the joints according to the calculated movement to effect the desired end effector movement. To provide increased range of motion for the various other types of movements described above, the system may include a revolute proximal most joint that affects the pitch of a distal instrument shaft of the manipulator and/or a distal revolute joint coupling an instrument to a proximal portion of the manipulator arm that effects a pivotal movement of the instrument shaft. In some embodiments, one or both of these joints may also be utilized in any of the clutch modes described herein.

In another aspect of the invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft passes through an access site. A processor having a controller couples the input device to the manipulator. Typically, in the tissue manipulator mode, in response to receiving a manipulation command to effect a desired end effector's movement, the system calculates end effector displacing movement of the joints, comprising calculating joint velocities within a null-perpendicular-space of the Jacobian orthogonal to the null-space, and drives the joints according to the calculated movement to effect the desired end effector movement in which the instrument shaft pivots about the remote center. In a clutch mode, the processor determines movements of one or more joints to float the first set of joints to allow a patient-side assistant to move an intermediate portion of the instrument within the access site and maintains the desired remote center location about which the shaft pivots. It is appreciated that this is but one of many variations of the clutch mode in accordance with the principles of the present invention and the clutch made may configured to float one or both of the tool tip or distal end effector and a remote center about which the end effector pivots while various other joints are maintained at a desired state. In addition, it is appreciated that various clutch modes may be concurrently used in order to effect various other tasks as needed.

In some embodiments, a first joint from the first set of joints of the manipulator is a revolute joint coupling the manipulator arm to the base. The desired state of the end effector may include a desired position, velocity or acceleration of the end effector. In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at a remote center if applicable. The system further includes a processor having a controller coupling the input to the manipulator arm and configured to calculate a movement of the plurality of joints in response to a user input command. The system may include a clutch mode in which a first set of joints of the plurality of joints float within a null-perpendicular space to allow a patient side assistant to move the end effector or a remote center about which the end effector moves to a desired position for surgery while one or more joints of a second set of joints are driven within a null-space according to one or more algorithms to effect various tasks, such as collision avoidance, pose preference, or to improve conditioning of the manipulator arm. In any of the embodiments described herein, each of the first and second set of joints may include one or more joints and the first and second joints may include one or more joints in common or may be entirely different sets of joints.

A further understanding of the nature and advantages of the present invention will become apparent by reference to the remaining portions of the specification and drawings. It is to be understood, however, that each of the figures is provided for the purpose of illustration only and is not intended as a definition of the limits of the scope of the invention. Furthermore, it is appreciated than any of the features in any of the described embodiments could be modified and combined with any of various other features described herein or known to one of skill in the art and still remain within the spirit and scope of the invention.

BRIEF DESCRIPTION OF THE DRAWINGS

FIGS. 6A-6B show an exemplary manipulator arm in the pitch forward configuration and pitch back configurations, respectively.

FIG. 6C shows a graphical representation of the range of motion of the surgical instrument end effector of an exemplary manipulator arm, including a cone of silence or conical tool access limit zone in each of the pitch forward and pitch back configurations.

FIG. 9A schematically illustrates a highly flexible manipulator assembly having a clutch input switch so as to facilitate manual positioning of a surgical tool adjacent a minimally invasive aperture while a processor configures the manipulator joint in response to the manual backdriving movement.

FIGS. 9B and 9C schematically illustrate reconfiguring of the joints of the manipulator assembly within a range of alternative joint configurations during manual backdriving movement of the arm.

FIGS. 12A-12C show exemplary manipulator arms having a proximal joint that translates a proximal joint supporting the manipulator arm about a curved path.

DETAILED DESCRIPTION OF THE INVENTION

Figure 1A:
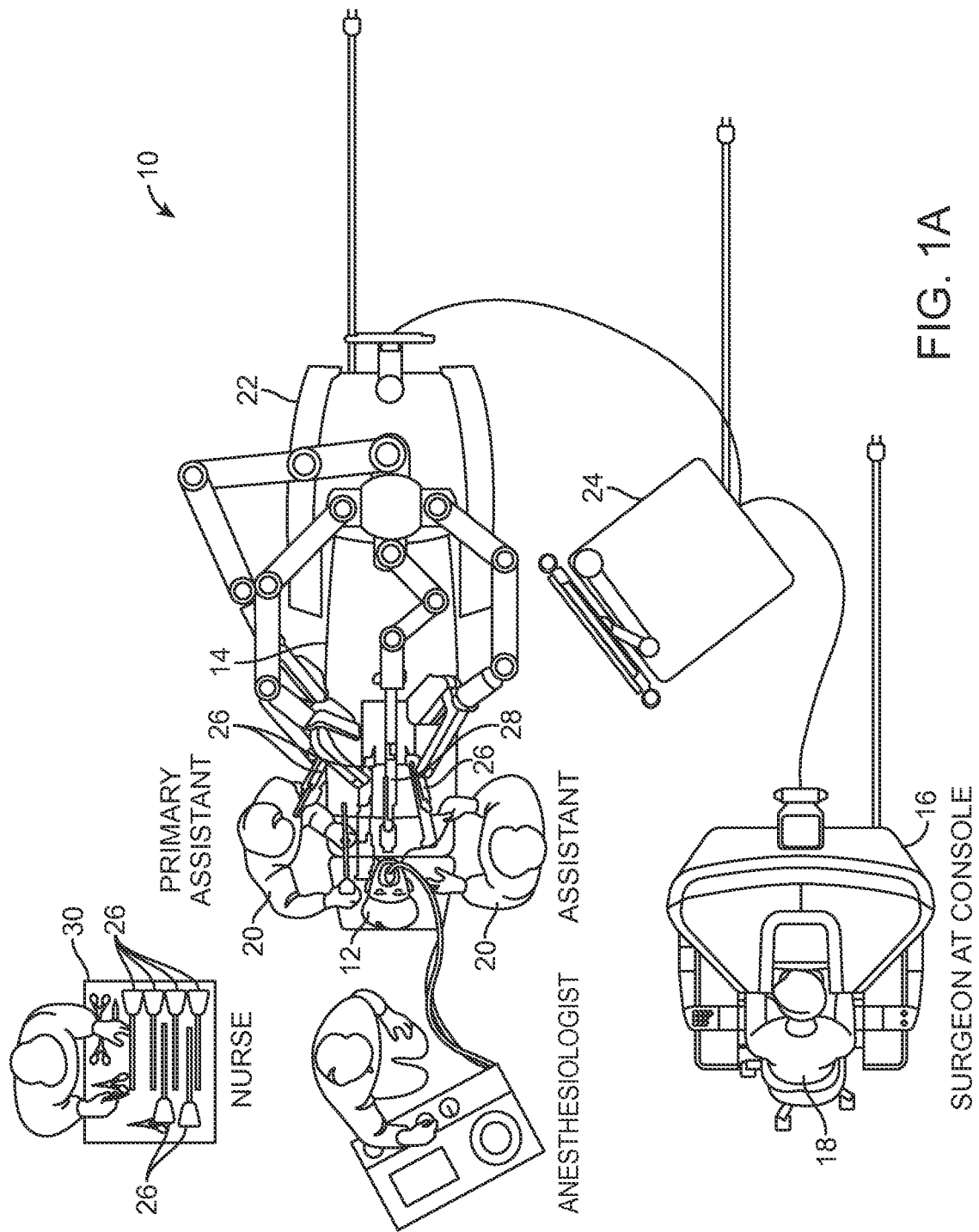
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments may be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allows a system operator, or an assistant, to reconfigure the linkages of the manipulator assemblies while maintaining the desired end effector state, optionally in preparation for surgery and/or while another use maneuvers the end effector during a surgical procedure. While aspects of the invention are generally described manipulators having redundant degrees of freedom, it is appreciated that aspects may apply also to non-redundant manipulators or a redundant arm approaching a singularity.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the exemplary manipulator assemblies described herein have more degrees of freedom than are needed to position and move an end effector within a surgical site. For example, a surgical end effector that can be positioned with six degrees of freedom at an internal surgical site through a minimally invasive aperture and may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In many embodiments, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein in its entirety. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with various aspects of the invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose, by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., movable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument, manual positioning of the links can be challenging and complicated. Even when the manipulator structure is balanced so as to avoid gravitational effects, attempting to align each of the joints in an appropriate arrangement or to reconfigure the manipulator as desired can be difficult, time consuming, and may involve significant training and/or skill. The challenges can be even greater when the links of the manipulator are not balanced about the joints, such that positioning such a highly configurable structures in an appropriate configuration before or during surgery can be a struggle due to the manipulator arm length and the passive and limp design in many surgical systems.

These issues can be addressed by allowing a user, such as a physician's assistant, to quickly and easily reconfigure the manipulator arm by floating one or more joints within a clutch mode. Repositioning a manipulator arm having floating joints, however, may present certain challenges. While the large number of redundant joints may provide increased range of motion for certain tasks, the additional joints in the manipulator arm may cause various movements of the arm to be overly complex during positioning or reconfiguration, such that the movements appear unpredictable or the amount of overall movements causes various other clinical concerns. To improve the movement of the manipulator arm, in many embodiments, the system drives a second set of joints within a null-space according to one or more null-space algorithms concurrent with floating the first set of joints so as to provide improved manipulator arm movement during manual positioning of the end effector by a user in the clutch mode. Examples of null-space movements that may be used in any of the clutch modes described herein are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
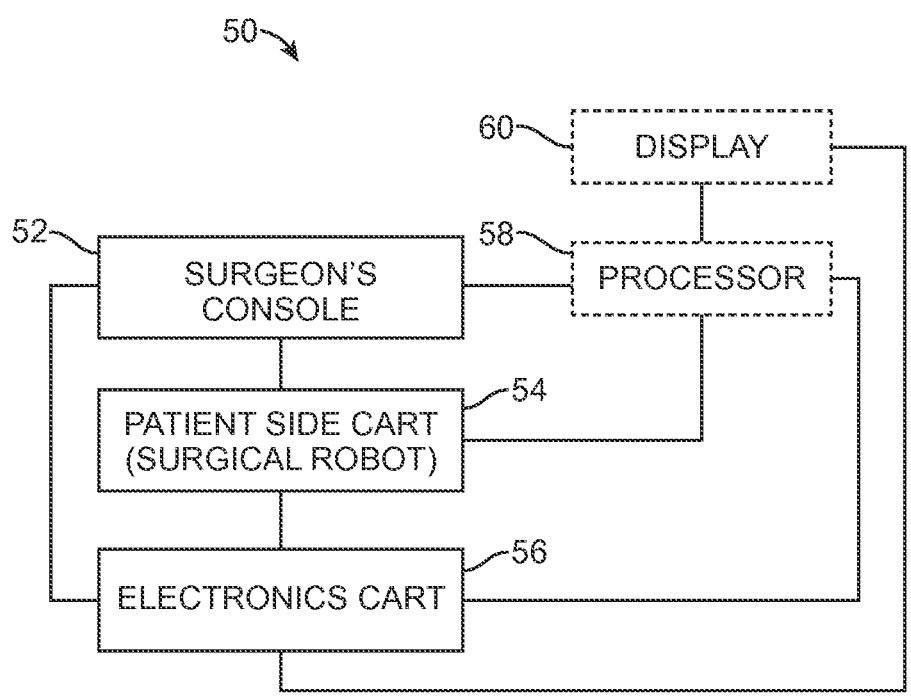
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a Surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
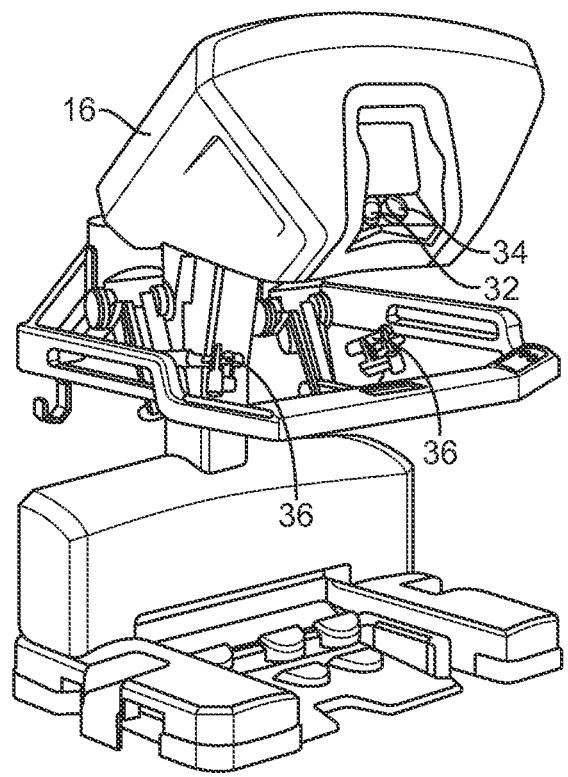
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1A) to manipulate one or more tools. The input control devices 36 can provide the same degrees of freedom as their associated tools 26 (shown in FIG. 1A) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
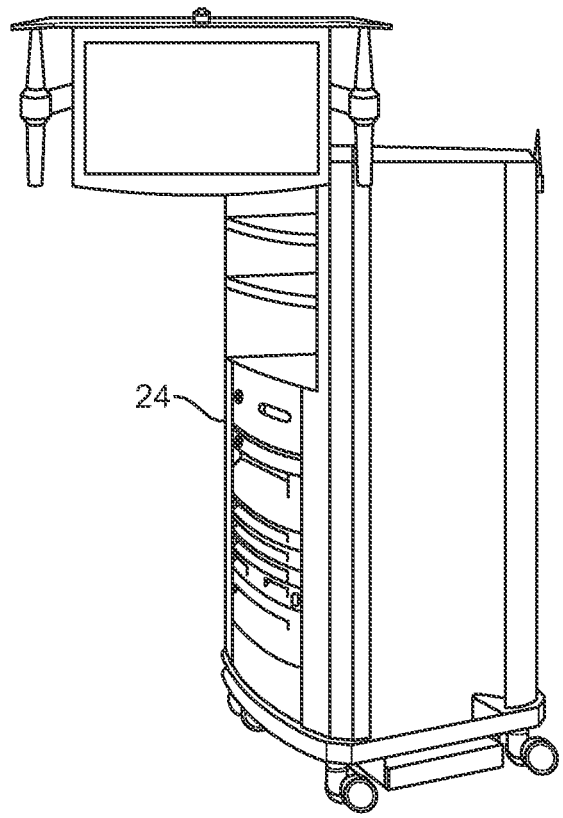
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
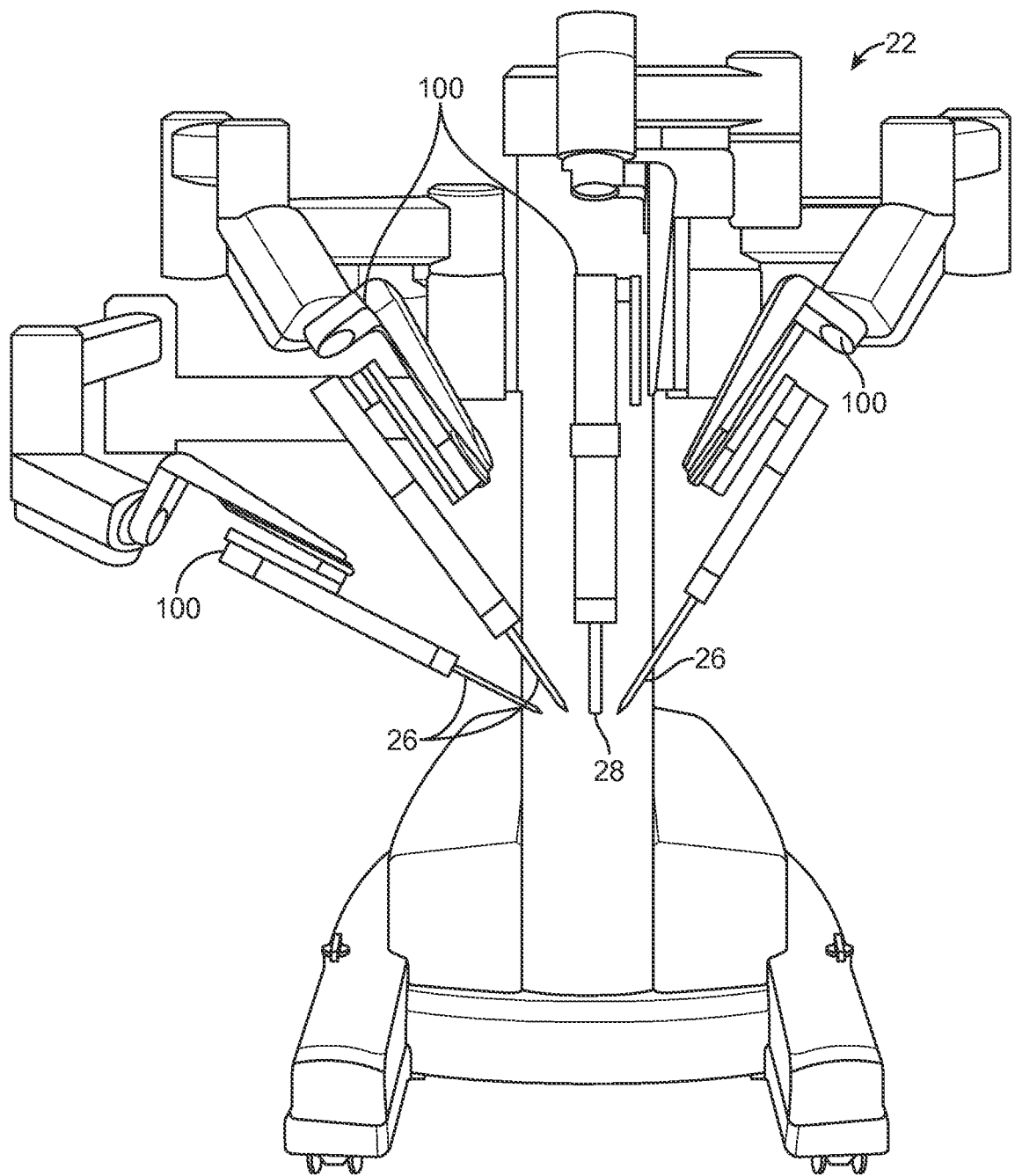
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-13C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
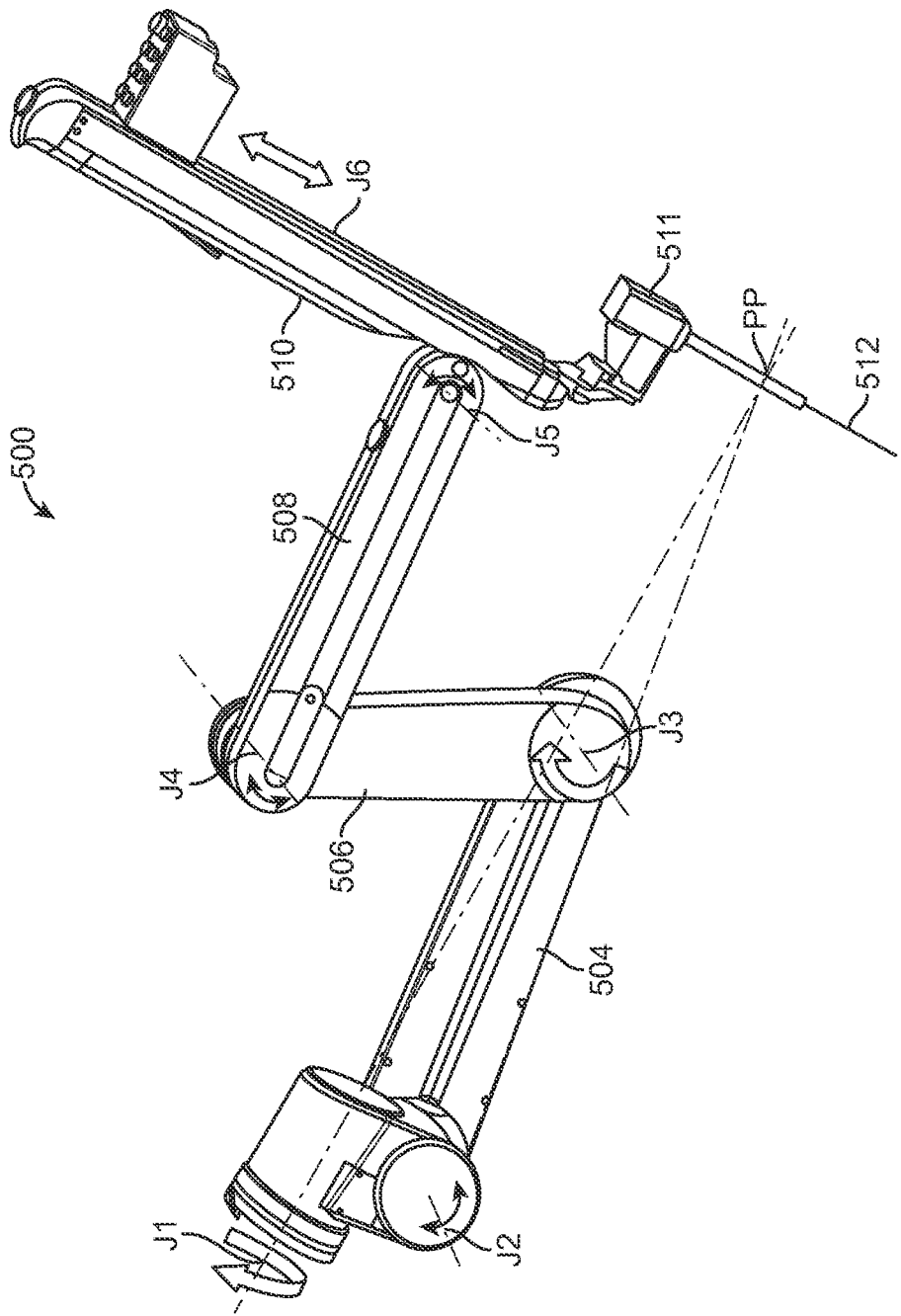
FIGS. 5A-5D show an exemplary manipulator arm.

In many embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
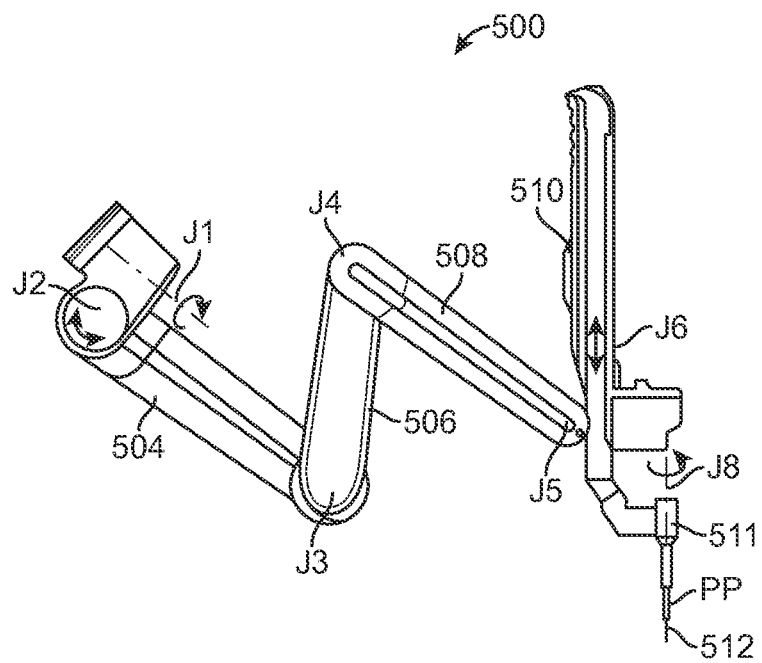
Figure 5D:
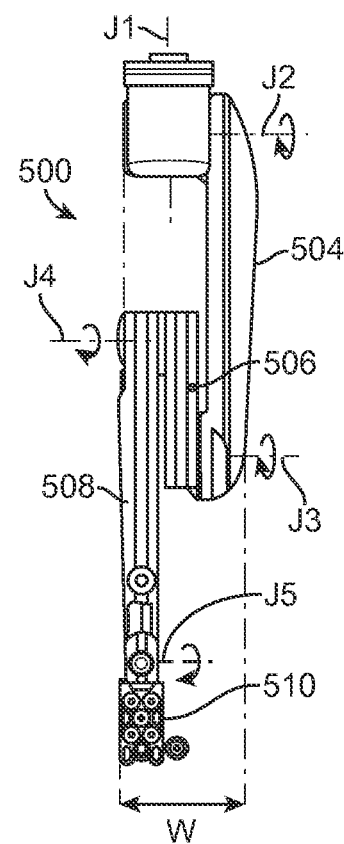
Figure 5C:
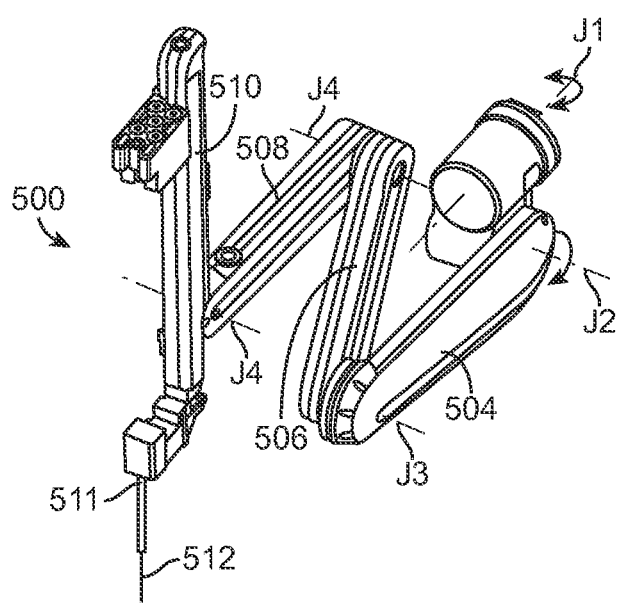

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In many embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J8 (not shown) near or proximal of the insertion point of the end effector or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (±75 degrees) for the outer pitch, and (±300 degrees) for the outer yaw joints, respectively. In some embodiments, the ROM may be increased for the outer pitch to provide a ROM larger than (±90 degrees) in which case the "cone of silence" could be made to disappear entirely, although generally the inner sphere associated with insertion limitations would remain. It is appreciated that various embodiments may be configured to have increased or decreased ROM, that the above noted ROMs are provided for illustrative purposed, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the end effector may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually backdriving one or more links of the manipulator to reconfigure the linkages and joints of the manipulator, which often requires an alternative operating mode and delays the surgical procedure.

Movement of the instrument shaft into or near these conical portions typically occurs when the angle between distal linkages in the manipulator is relatively small. Such configurations can be avoided by reconfiguring the manipulator to increase the angles between linkages (so that the linkages are moved into a more orthogonal position relative to each other).

For example, in the configurations shown in FIGS. 6A and 6B, when the angle between the distal most link and the instrument holder (angle α) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement.

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the end effector so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator end effector during manual positioning of the end effector in the clutch mode. The use and advantages of such additional joints can be understood by referring to FIGS. 7A-13C, which illustrate examples of such joints, which may each be used independent of one another or used in combination, in any of the exemplary manipulator arms described herein.

Figure 7A:
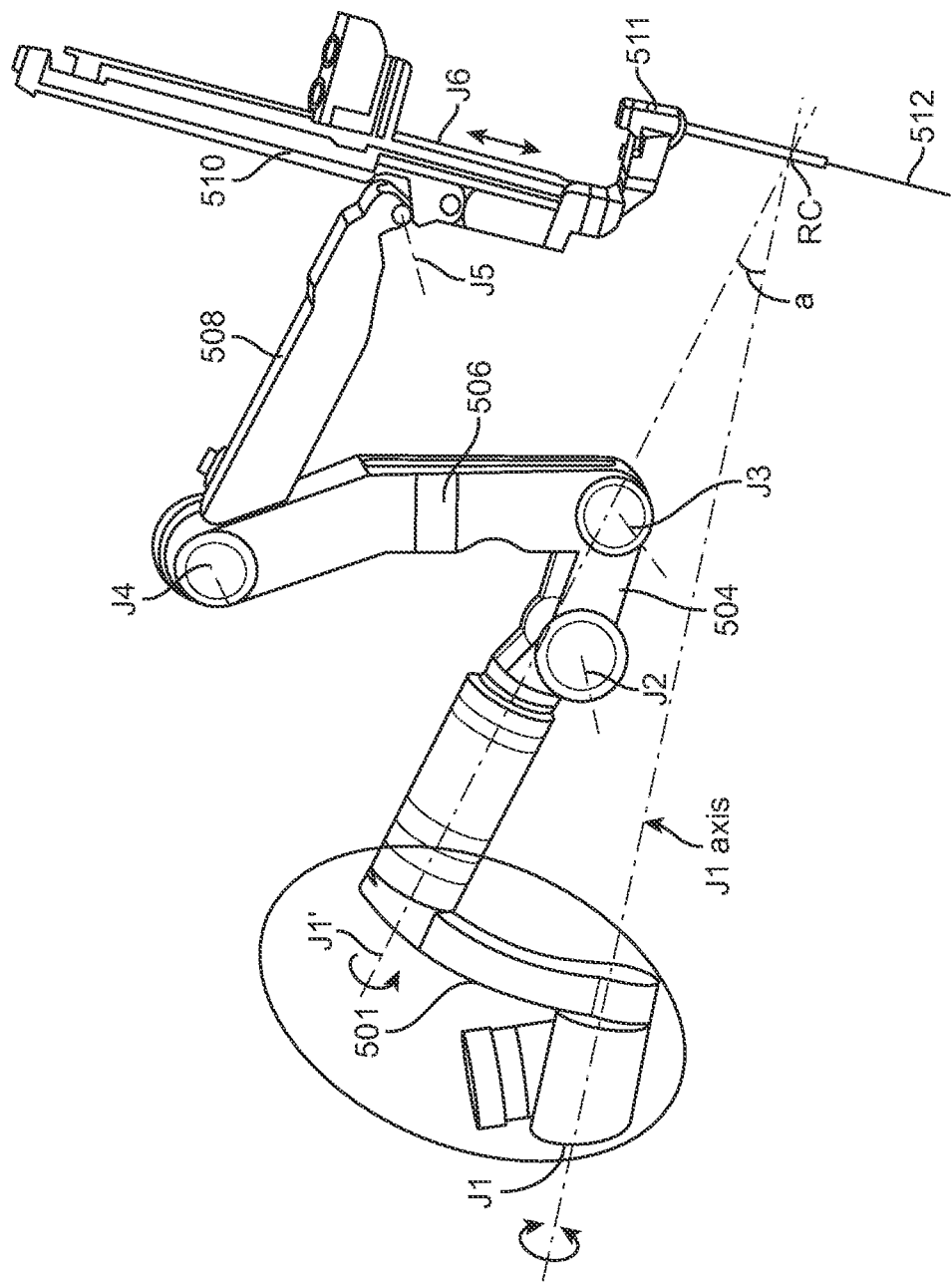
FIG. 7A shows exemplary manipulator arms having a proximal revolute joint that revolves the manipulator arm about an axis of a proximal revolute joint.
Figure 7B:
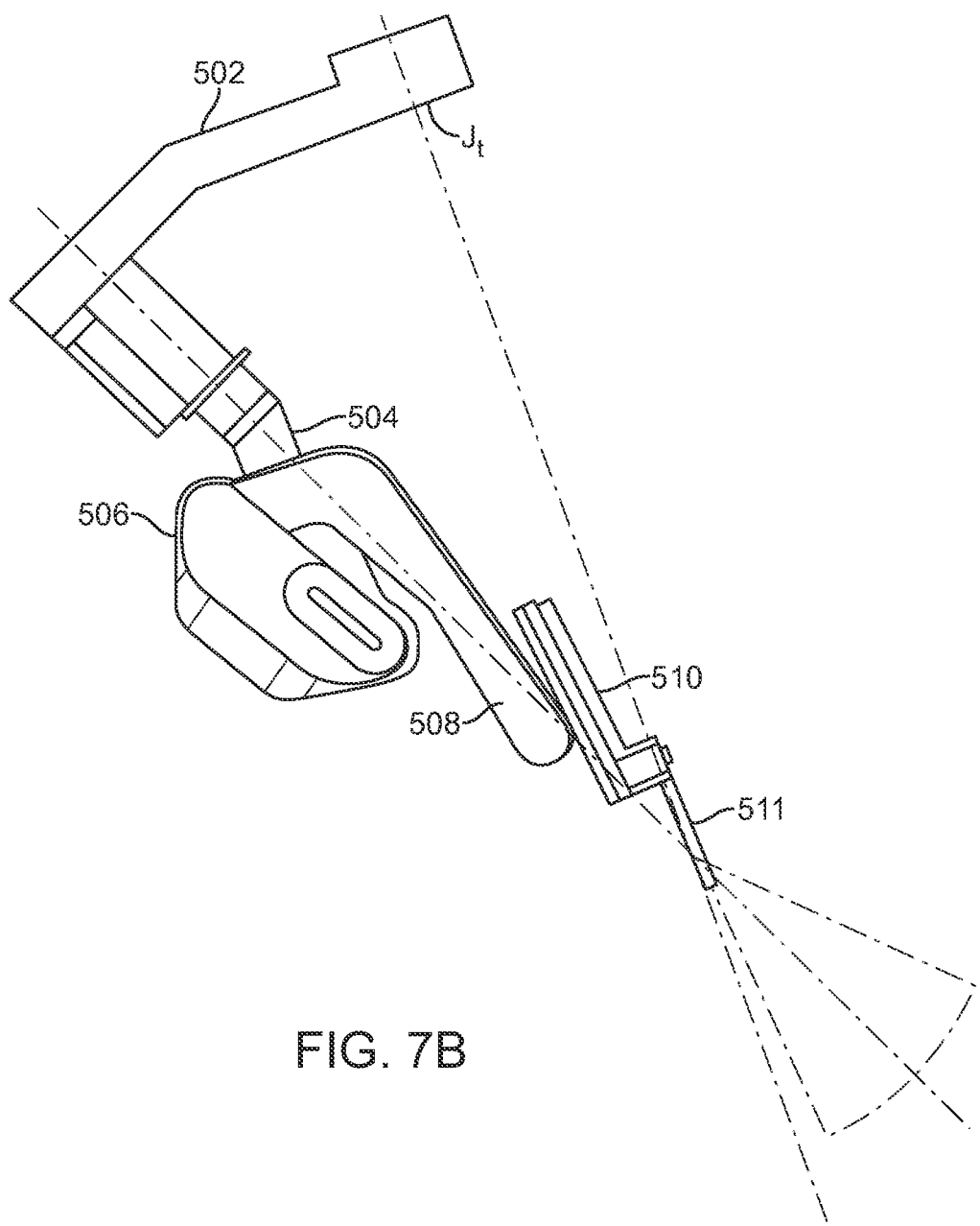
FIG. 7B shows an exemplary manipulator arm and the associated range of motion and cone of silence, the exemplary manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint J1' that revolves the manipulator arm about a joint axis of joint J1'. The proximal revolute J1' includes a link 501 that offsets joint J1 from the proximal revolute J1' by a pre-determined distance or angle. The link 501 can be a curved linkage, as shown in FIG. 7A, or a linear or angled linkage, as shown in FIG. 7B. Typically, the joint axis of the joint J1' is aligned with the remote center RC or insertion point of the end effector, as shown in each of FIG. 7A. In an exemplary embodiment, the joint axis of joint J1' passes through the remote center, as does each other revolute joint axis in the manipulator arm, to prevent motion at the body wall and can therefore be moved during surgery. The axis of joint J1' is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy and can also be used in the various clutch modes to provide such movement during manual positioning or docking of the end effector during set-up. In one aspect, the proximal revolute J1' is used solely to change the mounting angle of the manipulator with respect to the floor. This angle is important in order to 1) avoid collisions with external patient anatomy and 2) reach anatomy inside the body. Typically, the angle α between the proximal link of the manipulator attached to the proximal revolute joint J1' and the axis of the proximal revolute is about 15 degrees.

FIG. 7B illustrates the relationship of the proximal revolute joint J1' and its associated joint axis and the cone of silence in an exemplary manipulator arm. The joint axis of the proximal revolute joint J1' may pass through the cone of silence or may be completely outside of the cone of silence. By revolving the manipulator arm about the axis of the proximal revolute J1', the cone of silence can be reduced (in an embodiment where the joint J1' axis passes through the cone of silence), or can be effectively eliminated (in an embodiment where the proximal revolute joint axis extends completely outside the cone of silence). The distance and angle of the link 501 determines the position of the joint J1' axis relative to the cone of silence.

Figure 8A:
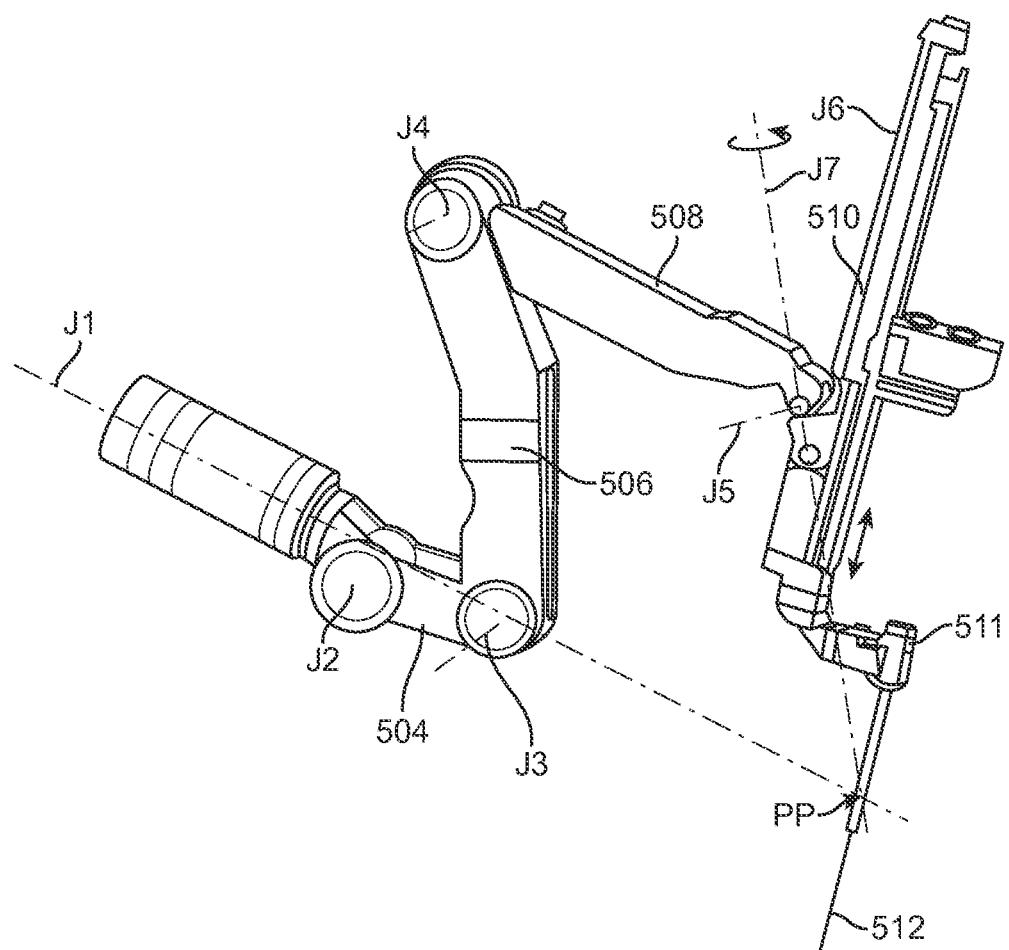
FIGS. 8A-8B show an exemplary manipulator arms having a revolute joint near the distal instrument holder.
Figure 8B:
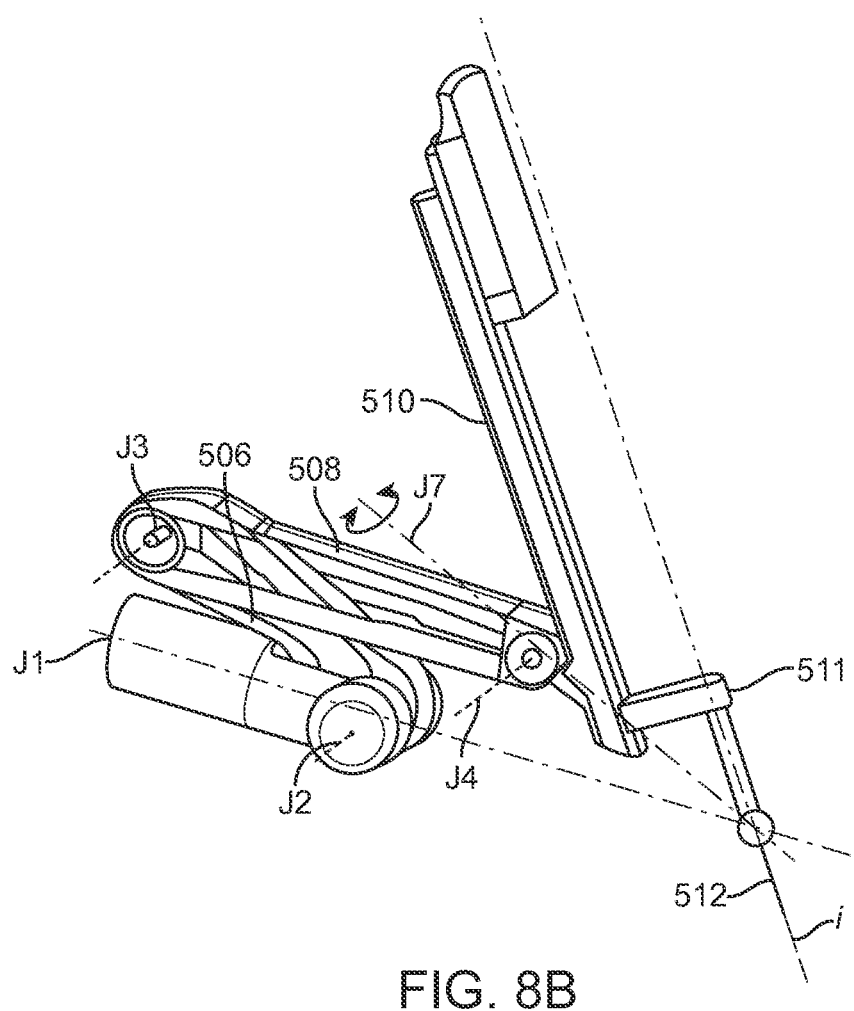
Figure 10A:
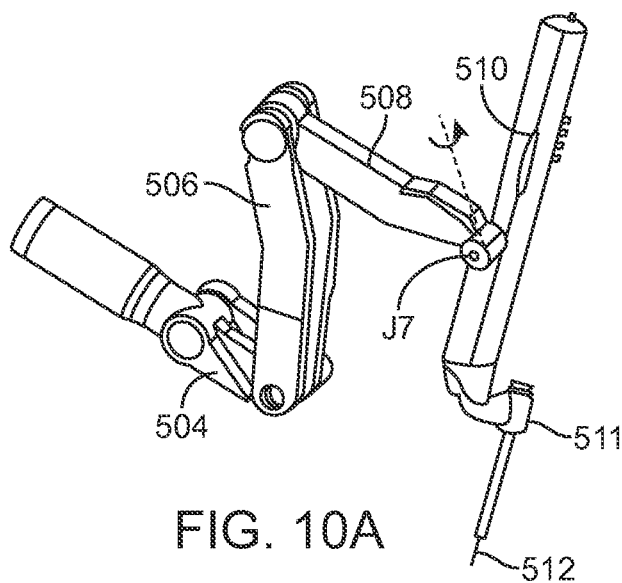
FIGS. 10A-10C show sequential views of an exemplary manipulator arm having a revolute joint near a distal instrument holder as the joint is moved throughout its range of joint movement.
Figure 10B:
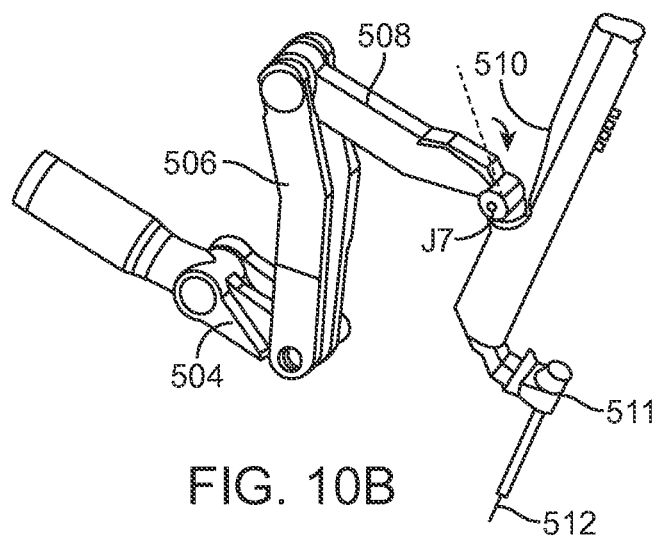
Figure 10C:
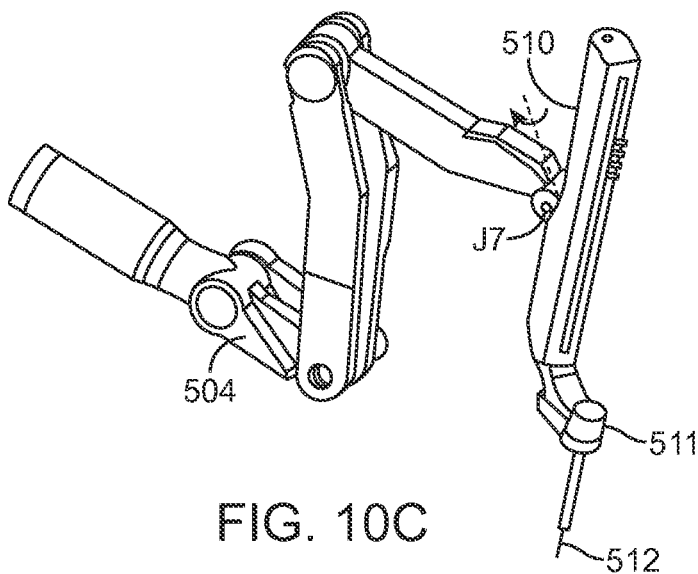

FIGS. 8A-8B illustrates another type of redundant joint for use with exemplary manipulator arms, a distal revolute joint J7 coupling the instrument holder 510 to a distal link of the manipulator arm 508. The distal revolute joint J7 allows the system to laterally pivot or twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase the range of motion when the manipulator arm is in a pitch back position. The relationship between the axis of the distal revolute joint J7, the yaw axis of J1 and the insertion axis of end effector is shown in FIG. 8B. FIGS. 10A-10C show the sequential movement of joint J7 and how movement of joint J7 shifts the insertion axis of end effector from side to side.

Referring now to FIG. 9A, another alternative manipulator assembly 520 includes a manipulator linkage arm 522 for removably supporting a surgical tool 524. A clutch input 516 comprises an input button which can be actuated by a hand engaging a link 518 of the manipulator that is to be disposed adjacent to access site 514 during surgery. This allows the hand to both actuate the input and help maneuver the manipulator into the appropriate position for surgery. In some embodiments, additional clutch inputs may be mounted on various other links so as to allow manual articulation of a link on which the clutch input is disposed. In many embodiments, the link 518 on which clutch input 516 is coupled to a shaft of a removable tool by an axial insertion joint. In one aspect, the system is configured such that the hand which actuates the clutch input 516 may also reposition the manipulator in the clutch mode without assistance from another hand. In another aspect, repositioning of the manipulator may be facilitated by having a user position both a first hand on the manipulator link 518 adjacent clutch input 516 and a second hand at a distance from the clutch input, particularly when reorienting the link to a desired axial insertion angle. In certain embodiments, while clutch input 516 is actuated by the hand, the system processor will float the first set of joints of manipulator 520 to allow manual backdriving movement of link 518 to a desired position, while the second set of joints is driven in a null-space to provide a desired movement of the proximal portion of the manipulator without otherwise interfering with manual positioning of link 518.

If the clutched degrees of freedom of the slave manipulator linkage coincide with one or more joint degrees of freedom (that is, if some joints are locked and some joints are free to move in the clutch mode), then clutching is direct: one simply turns off the controller for those joints that are free to move. However, it will often be advantageous to clutch joints in a dependent way, where motion of one joint is linked by the controller to motion of at least one other joint so that they can be manually articulated together as a single degree of freedom. This may be achieved by driving at least one joint of a robotic manipulator assembly in response to external articulation of at least one other joint. The controller can effect this motion, which will often be different than any degree of freedom of the mechanical system, by defining any desired arbitrary linear combination of joints that can be treated as a single degree of freedom that the operator may manipulate, optionally while some or all of the other mechanical degrees of freedom remain locked. This general concept includes port clutching, instrument clutching, elbow clutching (in which an intermediate elbow is allowed to move, for example, from an upward oriented apex configuration around to a laterally oriented apex configuration while a state of the end effector is maintained), and other clutching modes.

Various clutching modes and clutching behaviors may be included in any of the manipulators described herein, including for example in nonredundant hardware center arms, hardware center arms having redundant degrees of freedom and software center arms. In one aspect, the various clutching modes and clutching behaviors may be used separately, while in other aspect, any of the various clutch modes or clutch features may be used in combination with one another. For example, the manipulator system may include an arm-clutch mode and a port-clutch mode. These clutch modes allow a user to perform various tasks while effecting various other tasks or desired movements. For example, the arm-clutch mode may allow a user, such as the patient-side assistant, to back-drive the arm into a desired state and the port-clutch mode may allow a user to move a port through which the instrument extends. These modes may be combined so as to allow a patient-side assistant to back-drive the arm to a desired state while concurrently moving the port through which the instrument extends. In some embodiments, upon exiting the various clutch modes or features, a "following" state commences from the new arm state provided by the clutch mode(s) or clutch feature(s). Thus, a clutch mode may be a combination of various clutching modes or clutching features or behaviors, a variety of which are set forth in detail below.

Referring now to FIGS. 9A and 9B, manipulator assembly 502 may be reconfigured by the processor for any of a variety of differing reasons. In one aspect, a joint 526 may be driven from a downward oriented apex configuration to an upward oriented apex configuration so as to inhibit collisions with an adjacent arm, equipment, or personnel or to enhance a range of motion of the end effector 508. Some, but not all, of these changes in configuration of the manipulator assembly may be in response to external forces applied to the manipulator assembly, with the processor often driving a different joint of the manipulator than that which is being acted upon by the external force. For example, a manipulator arm movements may be effected in response to physiological movement of the patient such as patient breathing or the like or in response to repositioning of the patient, such as by reorienting a surgical table, and the like. In another aspect, the processor may reconfigure the manipulator assembly in response to calculations performed by the processor. In either aspect, the processor may vary from a simple master-slave controller so as to drive manipulator assembly in response to a signal so as to provide a preferred manipulator assembly configuration. Such configuring of the manipulator assembly may occur during master-slave end effector movements, during manual or other repositioning of the manipulator assembly, and/or at least partly at a different time, such as after releasing a clutch input. In many clutch modes, such movement is effected concurrently or simultaneously with floating of one or more joints (or alternatively one or both of the end effector and remote center) within the null-perpendicular space.

In one aspect, the null-space movement of the arm may be calculated in accordance with a set of constraints to effect movement along a desired path in a first mode, while floating one or more joints (which may include floating of one or both of the end effector and remote center) within the null-perpendicular space as described above. This allows at least a portion of the manipulator arm to move according to a desired movement, such as to improve conditioning of the arm, while another portion of the manipulator arm, such as a set-up joint, end effector, or remote center location, is moved by the user to a desired position.

Figure 11A:
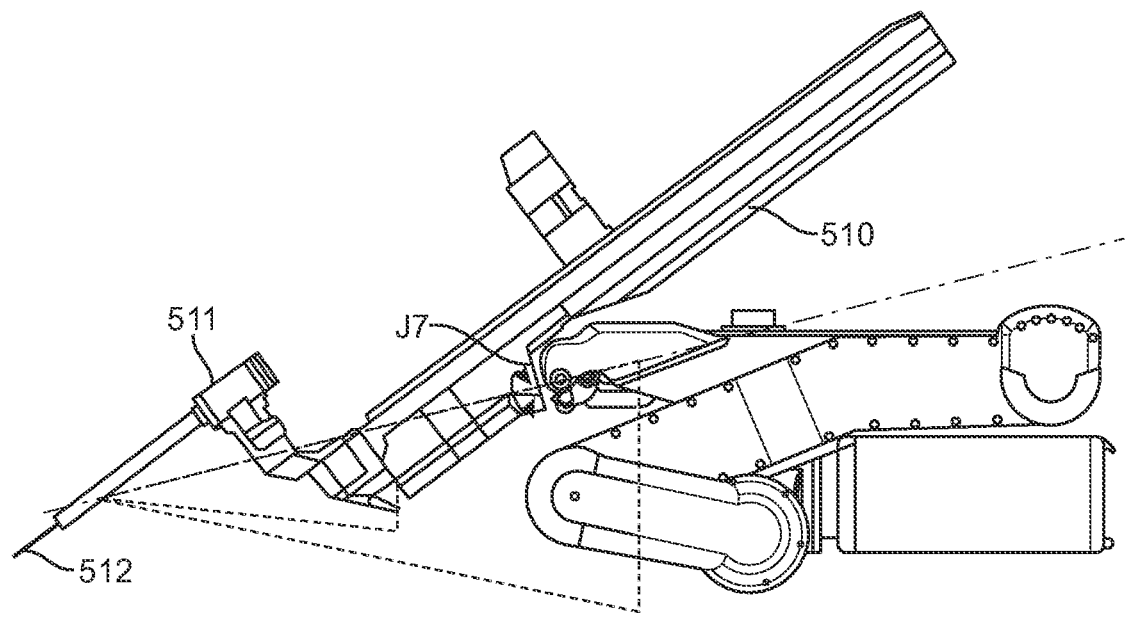
FIGS. 11A-11B show the revolved profile of an exemplary manipulator arm having a distal revolute joint when the angular displacement of the joint is 0° versus an angular displacement of 90°, respectively.
Figure 11B:
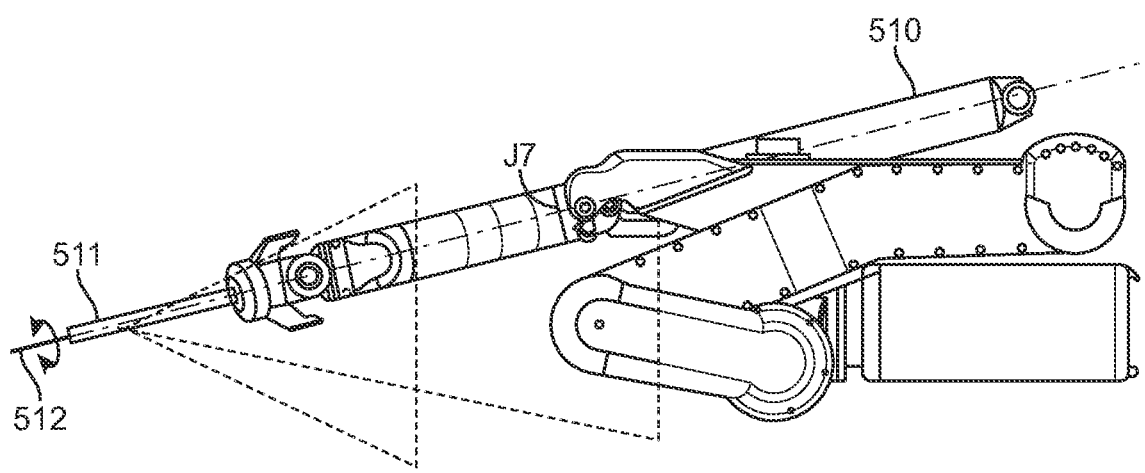

One advantage of the distal revolute joint J7 is that it may be used to reduce the patient clearance cone, which is the swept volume of the distal portion of the manipulator arm proximal of the insertion point that must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

Figure 13A:
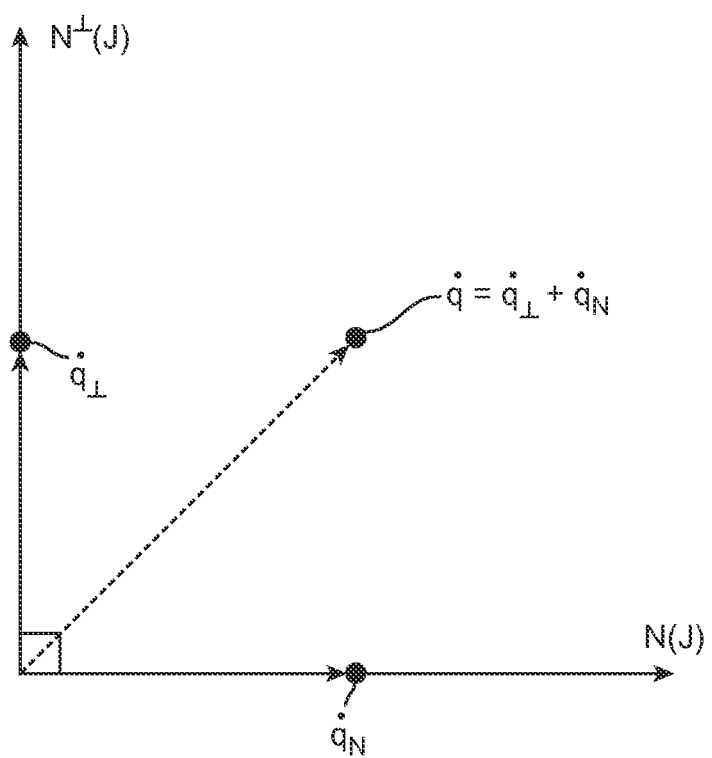
FIGS. 13A-13B graphically represent the relationship between the null-space and the null-perpendicular-space of the Jacobian of an exemplary manipulator assembly.
Figure 13B:
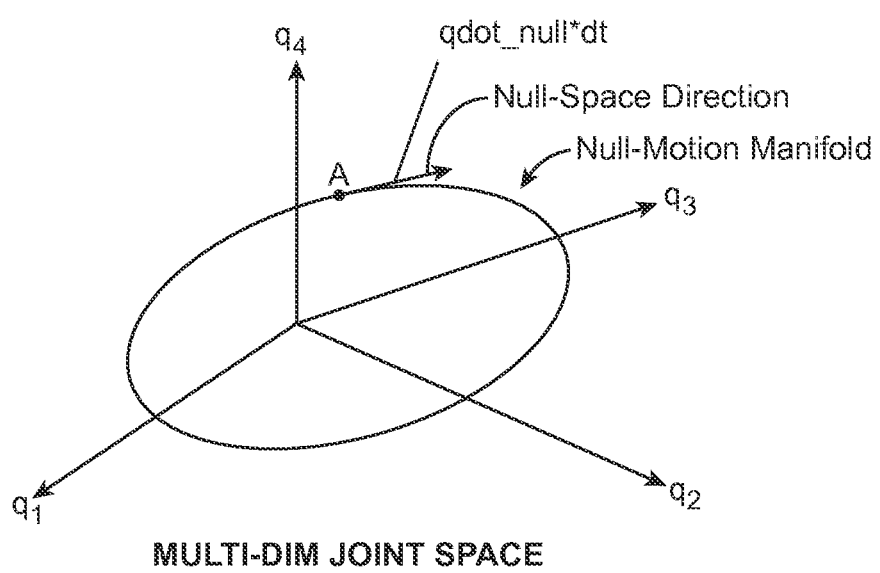

FIGS. 12A-12C illustrate another type of redundant joint for use with exemplary manipulator arms, a proximal joint that translates or revolves the manipulator arm about an axis. In many embodiments, this proximal translatable joint translates a proximal joint of the manipulator, such as joint J1 or J1', along a path so as to reduce or eliminate the cone of silence by shifting or rotating the range of motion of the manipulator arm to provide for better conditioning and improved maneuverability of the manipulator arm. The translatable joint may include a circular path, such as shown in joint J1" in FIGS. 12A-12D, or may include a semi-circular or arcuate path, such as shown in FIGS. 13A-13C. Generally, the joint revolves the manipulator arm about an axis of the translatable joint that intersects with the remote center RC about which the shaft of the tool 512 extending through cannula 511 pivots. Although in the embodiment shown in FIGS. 12A-12C, the axis of J1" is a vertical axis, although in some embodiments, the axis of J1" may be horizontal or various angles of inclination.

In certain embodiments, the manipulator arm 500 may include any or all of a proximal or distal revolute joint, a proximal translatable joint and a parallelogram configuration of the distal linkages. Use of any or all of these features provide additional redundant degrees of freedom and provide a desired movement of the manipulator arm concurrent with manually backdriving the distal end effector or remote center so as to provide for a better "conditioned" manipulator assembly by increasing the angles between linkages thereby improving the dexterity and motion of the manipulator during re-positioning and upon exiting of the clutch mode. The increased flexibility of this exemplary manipulator can also be used to optimize the kinematics of the manipulator linkage so as to avoid joint limits, singularities, and the like.

In certain embodiments, the joint movements of the manipulator are controlled by driving one or more joints with a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint velocity sub-space. The joint velocity sub-space may, for example, have as many dimensions as the manipulator has degrees of freedom, and a particular configuration of the manipulator may represent a particular point in the joint velocity sub-space, with each coordinate corresponding to a joint state of an associated joint of the manipulator.

In an exemplary embodiment, the system includes a controller in which a commanded position and velocity of a feature in the work-space, denoted here as its Cartesian space, are inputs. The feature may be any feature on or off the manipulator, which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\, dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\, \Delta x \quad (1)$$

$$dq/dt = J^\# dx/dt \quad (2)$$

$$q_i = q_{i-1} + dq/dt\, \Delta t \quad (3)$$

The pseudo-inverse of the Jacobian (J) directly maps the desired end effector motion (and, in some cases, a remote center of pivotal tool motion) into the joint velocity space. If the manipulator being used has more useful joint axes than end effector degrees of freedom (e.g. up to six), then the manipulator is said to be redundant. For example, when a remote center of tool motion is in use, the manipulator should have an additional 3 joint axes for the 3 degrees of freedom associated with location of the remote center. A redundant manipulator's Jacobian includes a "null-space" having a dimension of at least one. In this context, the "null-space" of the Jacobian (N(J)) is the space of joint velocities which instantaneously achieves no end effector motion (and when a remote center is used, no movement of the pivotal point location); and "null-motion" is the combination, trajectory or path of joint positions which also produces no instantaneous movement of the end effector and/or location of the remote center. Incorporating or injecting the calculated null-space velocities into the control system of the manipulator to achieve a desired reconfiguration of the manipulator changes above equation (2) to the following:

$$dq/dt = dq_{perp}/dt + dq_{null}/dt \quad (4)$$

$$dq_{perp}/dt = J^\# dx/dt \quad (5)$$

$$dq_{null}/dt = (1 - J^\# J)z = V_n V_n^T z = V_n \alpha \quad (6)$$

The joint velocity according to Equation (4) has two components: the first being the null-perpendicular-space component, the "purest" joint velocity (shortest vector length) which produces the desired end effector motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an exemplary system, wherein ($V_n$) is the set of orthonormal basis vectors for the null-space, and ($\alpha$) are the coefficients for blending those basis vectors. In some embodiments, $\alpha$ is determined by control parameters, variables or settings, such as by use of knobs or other control means, to shape or control the motion within the null-space as desired.

FIG. 13A graphically illustrates the relationship between the null-space of the Jacobian and the null-perpendicular-space of the Jacobian. FIG. 13A shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above.

FIG. 13B graphically illustrates the relationship between the null-space and the null-motion manifold within a four-dimensional joint space, shown as the "null-motion manifold." Each arrow (q1, q2, q3, and q4) representing a principal joint axis. The closed curve represents a null-motion manifold which is a set of joint-space positions which instantaneously achieves the same end effector position. For a given point A on the curve, since the null-space is a space of joint velocities which instantaneously produce no movement of the end effector, the null-space direction (ρ+A) is parallel to the tangent of the null-motion manifold at point A.

In manipulator arms having distal instruments that pivot about a remote center as determined by the hardware configuration, the manipulator arms typically include manipulator joints and set-up joints, the manipulator joints allowing commanded movement of the manipulator arm within a range of configuration and set-up joints. An example of a set-up joints include one or more revolute or pivotal joints attaching the manipulator arm to a proximal base movement of which may pivot or revolve the remote center within a range of movement of the set-up joints. In one aspect, the set-up joints are used to position the manipulator arm into a desired configuration prior to surgery (or to allow various desired movement during surgery), while the manipulator joints allow the surgeon to manipulate the arm and associated end effector to perform surgery. The set-up joints are not required to be fully motorized or drivable and may include joints that are manually adjusted during set-up, although the set-up joints may include fully drivable joints that are driven according to various algorithms. The various clutching features may include manipulator joints, set-up joints or both.

In certain embodiments, when the manipulator is in an arm-clutch mode, substantially all manipulator joints are allowed to float. It is appreciated, however, that when a joint is allowed to "float" torques may still be applied to compensate for gravity to allow the manipulator arm to be driven or manually backdriven to the desired state. When the manipulator is in the port-clutch mode, the manipulator set-up joints are allowed to float so that the remote center is released while torques remain applied to the manipulator joints (e.g. remain "servoed") so as to maintain the end effector at a controlled position (e.g. fixed position and/or orientation) while allowing the location of the port to be adjusted as desired. In a manipulator arm having a hardware remote center and non-redundant joints, when both the arm-clutch and port-clutch features are activated simultaneously, all the manipulator joints and manipulator set-up joints are released (e.g. allowed to "float").

In manipulators having manipulator joints with redundant degrees of freedom and a hardware remote center, the manipulator arm has a null-space of one or more dimensions (DIM=n, where n≥1). In some such manipulator arms, the set-up joints may include joints that are not fully motorized, such that the joint velocities discussed herein do not include the set-up joints. In addition to the clutching features described above, such manipulator arms may include various other clutch modes or features that utilize the redundant degrees of freedom of the manipulator joints. For example, some manipulators may include a null-clutch or null-float mode in which the manipulator joints are allowed to float along a null-space of the joints while maintaining a desired state of the tool tip and/or distal end effector. This allows the user or patient side assistant to reconfigure the manipulator arm proximal of the distal end effector, such as by driving one or more joints, or allows one for one or more various other tasks, such as collision avoidance.

In one aspect, a manipulator system in accordance with the present invention may include null-perpendicular clutch or null-perpendicular float that allows the end effector to float, while the movement of the joints within the null-space is controlled by any variety of null-space algorithms. This aspect allows the user or a patient-side assistant to backdrive (e.g. manually articulate) the end effector while various other features or algorithms relating to null-space movement are enacted (e.g. collision avoidance, commanded reconfiguration, tracking along a desired path within the null-space, emphasizing movement to control or increase range of movement of one or more joints, or any other movement pertaining to the null-space). Examples of such movements are described in further detail in the following applications: U.S. Provisional Application No. 61/654,755 filed Jun. 1, 2012, entitled "Manipulator Ann-to-Patent Collision Avoidance Using a Null-Space;" U.S. Provisional Application No. 61/654,764 filed Jun. 1, 2012, entitled "Commanded Reconfiguration of a Surgical Manipulator Using the Null-Space;" U.S. Provisional Application No. 61/654,773 filed Jun. 1, 2012, entitled "Systems and Methods for Avoiding Collisions Between Manipulator Arms Using a Null-Space;" each of which the entire contents are incorporated herein in their entirety for all purposes.

In manipulators having joints with redundant degrees of freedom where the location of the remote center is determined by software, the joints of the manipulator need not be classified as set-up joints versus manipulator joints. For example, in a manipulator arm having a hardware remote center, a minimum of three kinematic set-up joints degrees of freedom are required for positioning the remote center within a three-dimensional space and six kinematic manipulator degrees of freedom are requires for positioning and orienting the end effector in three-dimensional space. Additional joint degrees of freedom provide redundancies in either the set-up or manipulator kinematics. In a manipulator arm having a remote center determined by software, as opposed to a hardware remote center, the locating of the remote center and the positioning and orienting of the end effector may collectively be performed by the manipulator joints such that movement of the joints may contribute to both the set-up and manipulator kinematics without the use of distinct set-up joints and manipulator joints. Thus, to position each of the remote center and end effector within a three-dimensional space, at least nine kinematic degrees of freedom are needed in a general non-redundant software center manipulator arm. Additional joints beyond these result in redundancies in either the end effector, the remote center, or both. Further understanding of the joint space of such manipulators can be gained by referring to FIG. 14 discussed below.

Figure 14:
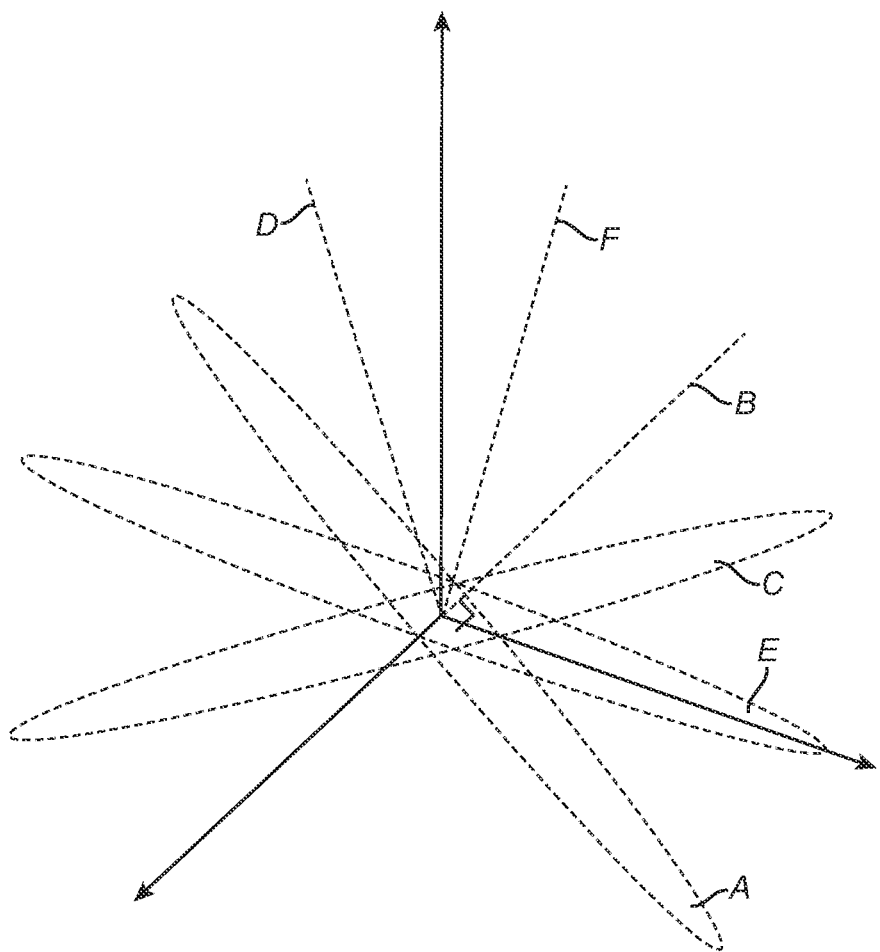
FIG. 14 graphically illustrates subspaces of the joint velocity space in a manipulator arm having a software remote center.

FIG. 14 graphically illustrates various sub-spaces of the n-dimensional joint velocity space of an example manipulator arm having a software remote center within the null-space (N) and the null-perpendicular space ($N^\perp$) being orthogonal to the null-space associated movement of the remote center (RC) and end effector (EE) and numbers of dimensions shown (DIM=n). The various subspaces illustrated are as follows:

Subspace A ($N^\perp(RC)$) is the null-perpendicular-space of the remote center, which is the subspace of joint velocities that result in motion of the remote center. Since the location of the remote center requires within the three-dimensional space requires three degrees-of-freedom, this subspace is three-dimensional.

Subspace B (N(RC)) is the null-space of the remote center, which is the subspace of joint velocities that result in no instantaneous motion of the remote center. This subspace is orthogonal to subspace A such that subspace B is (n−3) dimensional, where n is the dimension of the full joint velocity space (e.g. the total number of joints).

Subspace C ($N^\perp(EE)$) is the null-perpendicular-space of the end effector, which is the subspace of joint velocities that result in motion of the end effector. Since positioning and orienting the end effector requires three degrees-of-freedom for positions and three degrees-of-freedom for orientations, this subspace is six-dimensional.

Subspace D (N(EE)) is the null-space of the end effector, which is the subspace of joint velocities that result in no instantaneous motion of the end effector. This subspace is orthogonal to subspace C such that it is (n−6) dimensional.

Subspace E is the union or direct sum of subspace A and subspace C: $N^{\perp}(RC+EE)$: The subspace of joint velocities which result in motion of either the remote center, the end effector, or both. From the definitions of Subspace (A) and Subspace (C), this subspace is nine-dimensional.

Subspace F (N(RC+EE)) is the intersection of subspace B and subspace D, which is the subspace of joint velocities that results in no instantaneous motion of either the remote center or the end effector. This subspace is orthogonal to subspace E such that it is (n−9) dimensional.

The subspaces of a manipulator arm having a software remote center can be utilized by various other clutch modes, including but not limited to an arm-clutch mode, port-clutch mode, arm null-clutch mode, port null-clutch mode, arm null-perpendicular clutch mode, port null-perpendicular clutch mode, arm-port-null-perpendicular clutch mode, and arm-port-null-clutch mode, any mode described herein, or various combinations thereof. Certain clutch mode features are discussed in further detail below in reference to the examples subspaces illustrated in FIG. 14.

In one aspect, in order to make any of the port clutch behaviors clinically acceptable, the kinematics is likely to be set up with the distal end effector position and orientation defined relative to the remote center rather than the manipulator base. In such a case, when a port clutch is activated, and the remote center is floated and backdriven, presumably following a body wall, the end effector follows the back-driven port as well. This is in contrast to the case in which the kinematics of the end effector is defined relative to the base, in which case clutching the port would keep the end effector undesirably stationary. Using the former relative kinematic definition, the motion of the end effector relative to the entry at the body wall is minimized, which is desirable since the end effector may be interacting with anatomy.

In one aspect, the invention provides an arm-clutch mode or feature. The arm-clutch feature maintains a state of the remote center (e.g. the remote center is servoed) to allow the end effector to be repositioned by a user (e.g. patient-side assistant) by backdriving one or more joints, such as by manually articulating the end effector. The arm-clutch feature may be used by itself or concurrently with various other clutch features, such as the port-clutch feature described below. Typically, when the arm-clutch feature is used by itself, the Jacobian based controller is "servoing" within subspace A and floating along subspace B.

In another aspect, the invention provides an port-clutch mode or feature. The port-clutch features allowing the remote center to be repositioned by a user by backdriving one or more joints, such as by manual backdriving movement by a patient-side assistant. When the remote center is being repositioned, holding the end effector fixed in space is possible by servoing within the subspace C. However, a clinician would intuitively expect that the end effector doesn't move relative to the remote center. So when the port-clutch feature is used by itself, the Jacobian based controller is floating the joints between the base of the manipulator to the remote center, and servoing the joints from the remote center to the end effector.

The various clutch modes or features described herein may be utilized concurrently or simultaneously, including the arm-clutch and port-clutch features. In certain embodiments, simultaneously effecting the arm-clutch and port-clutch features floats all joints of the manipulator arm. An alternative means of implementing this feature is an arm-port-null-perpendicular clutch described below.

In another aspect, the invention provides a null-clutch mode or feature. The null-clutch feature keeps both the remote center and the end effector servoed, while allowing the manipulator joints to be repositioned by a user by backdriving one or more joints. In many embodiments, when this feature is used, the Jacobian based controller is servoing the joints within subspace E and floats the joints along subspace F.

In yet another aspect, the invention provides an arm-null-perpendicular-clutch mode or feature. The arm-null-perpendicular-clutch feature provides a desired behavior by (a) floating the end effector, (b) servoing the remote center, and (c) allowing the null-space algorithms to drive the joints. This is achieved by servoing along subspace A; floating along the subspace within subspace E which is orthogonal to subspace A; and allowing the null-space algorithms to drive along subspace F.

In another aspect, the invention provides a port-null-perpendicular-clutch mode or feature. The port-null-perpendicular-clutch feature provides the desired behavior by (a) servoing the end effector, (b) floating the remote center, and (c) allowing the null-space algorithms to drive the joints. This behavior is achieved by servoing the joints along subspace C; floating the joints along the subspace within subspace E which is orthogonal to subspace C; and allowing the null-space algorithms to drive along subspace F.

In yet another aspect, the invention provides an arm-port-null-perpendicular-clutch mode or feature. The arm-port-null-perpendicular-clutch features provides the desired behavior by (a) floating the end effector, (b) floating the remote center, and (c) allowing the null-space algorithms to drive the joints. This behavior is achieved by floating the joints along subspace E; and allowing the null-space algorithms to drive along subspace F.

Figure 15:
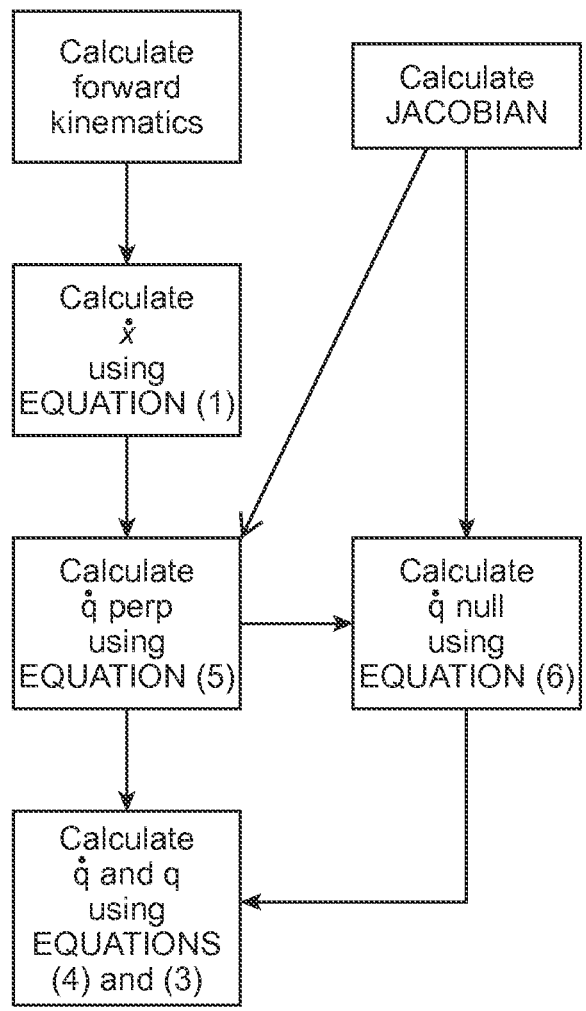
FIG. 15 schematically illustrates a method in accordance with many embodiments.
Figure 16:
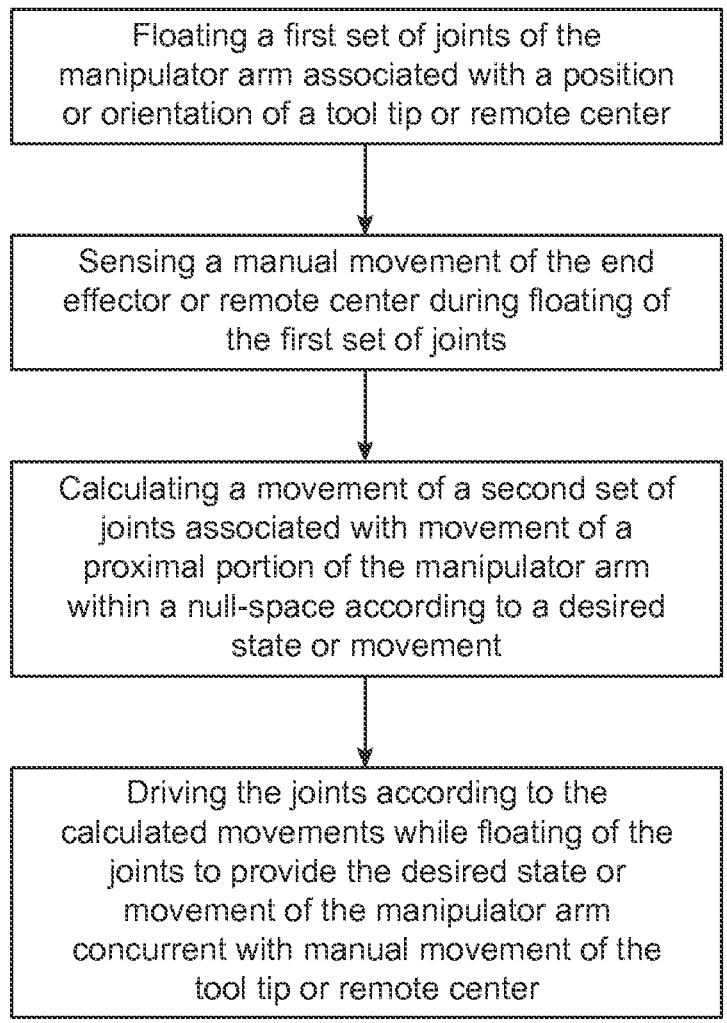
FIG. 16 illustrate example methods in accordance with many embodiments.

FIGS. 15-16 illustrate methods of reconfiguring a manipulator assembly of a robotic surgical system in accordance with many embodiments of the present invention. FIG. 15 shows a simplified schematic of the required blocks need to implement the general algorithms to control the patient side cart joint states, in relation to the equations discussed above. According to the method of FIG. 15, the system: calculates the forward kinematics of the manipulator arm; then calculates dx/dt using Equation (1), calculates $dq_{perp}/dt$ using Equation (5), then calculates $dq_{null}/dt$ from z, which may depend on $dq_{perp}/dt$ and the Jacobian using Equation (6). From the calculated $dq_{perp}/dt$ and $dq_{null}/dt$, the system then calculates dq/dt and q using Equations (4) and (3), respectively, thereby providing the movement by which the controller can effect the desired movement of the manipulator while maintaining the desired state of the end effector and/or location of the remote center during floating of the first set of joints and manual backdriving movement by the user.

FIG. 16 shows a block diagram of an example method for use in a robotic system. In the clutch mode depicted, the robotic system floats a first set of joints of the manipulator arm associated with a position or orientation of an end effector or remote center, senses a manual backdriving movement of the end effector or remote center during floating of the first set of joints, calculates a movement of a second set of joints associated with movement of a proximal portion of the manipulator arm within a null-space according to a desired state or movement, and drives the joints according to the calculated movements during floating of the joints to provide the desired state or movement of the manipulator arm concurrent with manual backdriving movement of the end effector or remote center. It can be appreciated that this method may include various aspects or features of any of the embodiments described herein.

While the exemplary embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A system comprising:
   a manipulator arm configured to support an instrument having an end effector, the manipulator arm comprising a distal portion, a proximal portion coupled to a base, and a plurality of joints between the distal portion and the base, the plurality of joints providing sufficient degrees of freedom to allow a range of differing joint states of the plurality of joints for a state of the distal portion; and
   a processor coupled to the manipulator arm, the processor configured with a manipulation mode and a first clutch mode, the first clutch mode selected from the group consisting of: an arm-null-perpendicular-clutch mode, a port-null-perpendicular-clutch mode, and an arm-port-null-perpendicular-clutch mode, wherein the processor is configured to perform operations comprising:
      in the manipulation mode, driving the plurality of joints to move an end effector of the instrument while pivoting the instrument about a remote center, and
      in the first clutch mode, operating the plurality of joints in accordance with the first clutch mode;
   wherein the arm-null-perpendicular-clutch mode corresponds to concurrently:
      servoing the plurality of joints in a null-perpendicular space of the remote center to maintain a position of the remote center,
      floating the plurality of joints in a first subspace while applying friction compensation or gravity compensation, the first subspace being a portion of a null-perpendicular space of the end effector orthogonal to the null-perpendicular space of the remote center, and
      controlling motion of the plurality of joints in an intersection of a null-space of the remote center and a null-space of the end effector;
   wherein the port-null-perpendicular-clutch mode corresponds to concurrently:
      servoing the plurality of joints in a null-perpendicular space of the end effector to maintain a position of the end effector,
      floating the plurality of joints in a second subspace while applying friction compensation or gravity compensation, the second subspace being a portion of the null-perpendicular space of the remote center orthogonal to the null-perpendicular space of the end effector, and
      controlling the motion of the plurality of joints in the intersection of the null-space of the remote center and the null-space of the end effector; and
   wherein the arm-port-null-perpendicular-clutch mode corresponds to concurrently:
      floating the plurality of joints in a union of the null-perpendicular space of the remote center and the null-perpendicular space of the end effector while applying friction compensation or gravity compensation, and
      controlling the motion of the plurality of joints in the intersection of the null-space of the remote center and the null-space of the end effector.

2. The system of claim 1, wherein the first clutch mode is the arm-null-perpendicular-clutch mode.

3. The system of claim 2, wherein the processor is further configured with a second clutch mode, the second clutch mode being the port-null-perpendicular-clutch mode, and wherein the operations further comprise:
   in the second clutch mode, operating the plurality of joints in accordance with the second clutch mode.

4. The system of claim 1, wherein the first clutch mode is the port-null-perpendicular-clutch mode.

5. The system of claim 1, wherein the first clutch mode is the arm-port-null-perpendicular-clutch mode.

6. The system of claim 1, wherein the first clutch mode is the arm-null-perpendicular-clutch mode, and wherein the processor is further configured with a second clutch mode and a third clutch mode, the second clutch mode being the port-null-perpendicular-clutch mode and the third clutch mode being the arm-port-null-perpendicular-clutch mode, and wherein the operations further comprise:
   in the second clutch mode, operating the plurality of joints in accordance with the second clutch mode, and
   in the third clutch mode, operating the plurality of joints in accordance with the third clutch mode.

7. The system of claim 1, wherein controlling the motion of the plurality of joints in the intersection comprises:
   controlling the motion of the plurality of joints in accordance with an auxiliary task.

8. The system of claim 7, wherein the auxiliary task comprises a task selected from the group consisting of: avoiding collision, achieving pose preference, conditioning the plurality of joints, and increasing range of motion.

9. The system of claim 1, wherein the processor is further configured with a simultaneous arm-clutch and port-clutch mode, and wherein the operations further comprise:
   in the simultaneous arm-clutch and port-clutch mode, concurrently floating all joints of the plurality of joints while applying friction compensation or gravity compensation.

10. The system of claim 1, wherein floating a joint of the plurality of joints in a joint subspace facilitates motion of the joint in the joint subspace by:
    zeroing out a torque of a motor associated with movement of the joint in the joint subspace; or
    setting a difference to zero, wherein the difference is between a measured position and a commanded position of the joint, or between a measured velocity and a commanded velocity of the joint.

11. A system comprising:
    a manipulator arm configured to support an instrument having an end effector, the manipulator arm comprising a distal portion, a proximal portion coupled to a base, and a plurality of joints between the distal portion and the base, the plurality of joints providing sufficient degrees of freedom to allow a range of differing joint states of the plurality of joints for a state of the distal portion; and
    a processor coupled to the manipulator arm, the processor configured with a manipulation mode and a first clutch mode, the first clutch mode selected from the group consisting of: an arm-clutch mode, a port-clutch mode, and a null-clutch mode, wherein the processor is configured to perform operations comprising:
       in the manipulation mode, driving the plurality of joints to move an end effector of the instrument while pivoting the instrument about a remote center, and
       in the first clutch mode, operating the plurality of joints in accordance with the first clutch mode;

wherein the arm-clutch mode corresponds to concurrently:
  servoing the plurality of joints in a null-perpendicular space of the remote center to maintain a position of the remote center, and
  floating the plurality of joints in a null-space of the remote center while applying friction compensation or gravity compensation;
wherein the port-clutch mode corresponds to concurrently:
  servoing the plurality of joints in a null-perpendicular space of the end effector to maintain a position of the end effector, and
  floating the plurality of joints in a null-space of the end effector while applying friction compensation or gravity compensation; and
wherein the null-clutch mode corresponds to concurrently:
  servoing the plurality of joints in a union space to maintain a position of the remote center and to maintain a position of the end effector, wherein the union space is a union of a null-perpendicular space of the remote center and a null-perpendicular space of the end effector, and
  floating the plurality of joints in an intersection of a null-space of the remote center and a null-space of the end effector while applying friction compensation or gravity compensation.

12. The system of claim 11, wherein the first clutch mode is the arm-clutch mode.

13. The system of claim 11, wherein the first clutch mode is the port-clutch mode.

14. The system of claim 11, wherein the processor is further configured with a second clutch mode, the second clutch mode being the null-clutch mode, and wherein the operations further comprise:
  in the second clutch mode, operating the plurality of joints in accordance with the second clutch mode.

15. The system of claim 11, wherein the first clutch mode is the arm-clutch mode, and wherein the processor is further configured with a second clutch mode and a third clutch mode, the second clutch mode being the port-clutch mode and the third clutch mode being the null-clutch mode, and wherein the operations further comprise:
  in the second clutch mode, operating the plurality of joints in accordance with the second clutch mode, and
  in the third clutch mode, operating the plurality of joints in accordance with the third clutch mode.

16. The system of claim 11, wherein the first clutch mode is the null-clutch mode.

17. A system processor configured for operating a system comprising a manipulator arm, wherein the manipulator arm is configured to support an instrument having an end effector, wherein the manipulator arm comprising a distal portion, a proximal portion coupled to a base, and a plurality of joints between the distal portion and the base, the plurality of joints providing sufficient degrees of freedom to allow a range of differing joint states of the plurality of joints for a state of the distal portion, wherein:
  the processor is configured with a manipulation mode and a first clutch mode, the first clutch mode selected from the group consisting of: an arm-null-perpendicular-clutch mode, a port-null-perpendicular-clutch mode, and an arm-port-null-perpendicular-clutch mode,
  the processor is further configured to perform a method comprising:
    in the manipulation mode, the processor driving the plurality of joints to move an end effector of the instrument while pivoting the instrument about a remote center, and
    in the first clutch mode, the processor operating the plurality of joints in accordance with the first clutch mode;
  wherein the arm-null-perpendicular-clutch mode corresponds to concurrently:
    the processor servoing the plurality of joints in a null-perpendicular space of the remote center to maintain a position of the remote center,
    the processor floating the plurality of joints in a first subspace while applying friction compensation or gravity compensation, the first subspace being a portion of a null-perpendicular space of the end effector orthogonal to the null-perpendicular space of the remote center, and
    the processor controlling motion of the plurality of joints in an intersection of a null-space of the remote center and a null-space of the end effector;
  wherein the port-null-perpendicular-clutch mode corresponds to concurrently:
    the processor servoing the plurality of joints in a null-perpendicular space of the end effector to maintain a position of the end effector,
    the processor floating the plurality of joints in a second subspace while applying friction compensation or gravity compensation, the second subspace being a portion of the null-perpendicular space of the remote center orthogonal to the null-perpendicular space of the end effector, and
    the processor controlling the motion of the plurality of joints in the intersection of the null-space of the remote center and the null-space of the end effector; and
  wherein the arm-port-null-perpendicular-clutch mode corresponds to concurrently:
    the processor floating the plurality of joints in a union of the null-perpendicular space of the remote center and the null-perpendicular space of the end effector while applying friction compensation or gravity compensation, and
    the processor controlling the motion of the plurality of joints in the intersection of the null-space of the remote center and the null-space of the end effector.

18. The system processor of claim 17, wherein:
  the first clutch mode is the arm-null-perpendicular-clutch mode;
  the processor is further configured with a second clutch mode, the second clutch mode being the port-null-perpendicular-clutch mode; and
  the method further comprises: in the second clutch mode, the processor operating the plurality of joints in accordance with the second clutch mode.

19. The system processor of claim 17, wherein the first clutch mode is the arm-null-perpendicular-clutch mode, wherein the processor is further configured with a second clutch mode and a third clutch mode, the second clutch mode being the port-null-perpendicular-clutch mode and the third clutch mode being the arm-port-null-perpendicular-clutch mode, and wherein the method further comprises:
  in the second clutch mode, the processor operating the plurality of joints in accordance with the second clutch mode, and in the third clutch mode, the processor operating the plurality of joints in accordance with the third clutch mode.

20. The system processor of claim 17, wherein the first clutch mode is the arm-port-null-perpendicular-clutch mode.

21. The system processor of claim 17, wherein the processor is further configured with a simultaneous arm-clutch and port-clutch mode, and wherein the method further comprises:
in the simultaneous arm-clutch and port-clutch mode, the processor concurrently floating all joints of the plurality of joints while applying friction compensation or gravity compensation.

22. A system processor configured for operating a system comprising a manipulator arm, wherein the manipulator arm is configured to support an instrument having an end effector, wherein the manipulator arm comprising a distal portion, a proximal portion coupled to a base, and a plurality of joints between the distal portion and the base, the plurality of joints providing sufficient degrees of freedom to allow a range of differing joint states of the plurality of joints for a state of the distal portion, and wherein:
the processor is configured with a manipulation mode and a first clutch mode, the first clutch mode selected from the group consisting of: an arm-clutch mode, a port-clutch mode, and a null-clutch mode; and
the processor is further configured to perform a method comprising:
in the manipulation mode, the processor driving the plurality of joints to move an end effector of the instrument while pivoting the instrument about a remote center, and
in the first clutch mode, the processor operating the plurality of joints in accordance with the first clutch mode;
wherein the arm-clutch mode corresponds to concurrently:
the processor servoing the plurality of joints in a null-perpendicular space of the remote center to maintain a position of the remote center, and
the processor floating the plurality of joints in a null-space of the remote center while applying friction compensation or gravity compensation;
wherein the port-clutch mode corresponds to concurrently:
the processor servoing the plurality of joints in a null-perpendicular space of the end effector to maintain a position of the end effector, and
the processor floating the plurality of joints in a null-space of the end effector while applying friction compensation or gravity compensation; and
wherein the null-clutch mode corresponds to concurrently:
the processor servoing the plurality of joints in a union space to maintain a position of the remote center and to maintain a position of the end effector, wherein the union space is a union of a null-perpendicular space of the remote center and a null-perpendicular space of the end effector, and
the processor floating the plurality of joints in an intersection of a null-space of the remote center and a null-space of the end effector while applying friction compensation or gravity compensation.

23. The system processor of claim 22, wherein:
the first clutch mode is the arm-clutch mode or the port-clutch mode;
the processor is further configured with a second clutch mode, the second clutch mode being the null-clutch mode; and
the method further comprises: in the second clutch mode, the processor operating the plurality of joints in accordance with the second clutch mode.

24. The system processor of claim 22, wherein the first clutch mode is the arm-clutch mode, wherein the processor is further configured with a second clutch mode and a third clutch mode, the second clutch mode being the port-clutch mode and the third clutch mode being the null-clutch mode, and wherein the method further comprises:
in the second clutch mode, the processor operating the plurality of joints in accordance with the second clutch mode, and
in the third clutch mode, the processor operating the plurality of joints in accordance with the third clutch mode.

25. The system processor of claim 22, wherein the processor is further configured with a simultaneous arm-clutch and port-clutch mode, and wherein the method further comprises:
in the simultaneous arm-clutch and port-clutch mode, the processor concurrently floating all joints of the plurality of joints while applying friction compensation or gravity compensation.

* * * * *